(12) United States Patent
Long et al.

(10) Patent No.: US 10,712,330 B2
(45) Date of Patent: Jul. 14, 2020

(54) CONTROLLING BITUMEN RECOVERY FROM AN OIL SANDS ORE BODY BY USING A PREDICTIVE ORE PROCESSABILITY MODEL IN PRODUCING A BLENDED ORE FEEDSTOCK

(71) Applicant: SYNCRUDE CANADA LTD. in trust for the owners of the Syncrude Project as such owners exist now and in the future, Fort McMurray (CA)

(72) Inventors: Jun Long, Edmonton (CA); Jonathan Spence, Edmonton (CA); Dean Wallace, Sorrento (CA); Shane Hoskins, Edmonton (CA); Chung H. Ta, Edmonton (CA); David Mueller, Edmonton (CA); Priyanka Pareek, Edmonton (CA)

(73) Assignee: SYNCRUDE CANADA LTD., Fort McMurray (CA), in trust for the owners of the Syncrude Project as such owners exist now and in the future ( * ) Notice: Subject to any disclaimer, the term of this patent is extended or adjusted under 35 U.S.C. 154(b) by 0 days.

(21) Appl. No.: 16/045,430

(22) Filed: Jul. 25, 2018

(65) Prior Publication Data

US 2020/0033316 A1 Jan. 30, 2020

(51) Int. Cl.
*G01N 33/28* (2006.01)
*C10G 1/04* (2006.01)
(Continued)

(52) U.S. Cl.
CPC .......... *G01N 33/2823* (2013.01); *B03D 1/02* (2013.01); *C10G 1/04* (2013.01); *C10G 1/047* (2013.01);
(Continued)

(58) Field of Classification Search
CPC ...... C10G 1/04; C10G 1/047; G01N 33/2823; G01N 33/241; E21C 41/31
See application file for complete search history.

(56) References Cited

U.S. PATENT DOCUMENTS

2013/0256196 A1* 10/2013 Spence ................. C10G 1/047
208/391
2014/0326885 A1* 11/2014 Davis .................. G01N 33/241
250/339.01
(Continued)

FOREIGN PATENT DOCUMENTS

| CA | 2 899 348 | * 10/2015 | ............. G01N 33/24 |
|---|---|---|---|
| CA | 2893161 C | 11/2016 | |
| CA | 2949425 C | 1/2017 | |

OTHER PUBLICATIONS

Wang, Yang et al, "Characterizing (Oil Sands) Ore Body with Process Performance Indicators using Pattern Recognition", Search and Discovery Article #40699, Feb. 2011, obtained from http://www.searchanddiscovery.com/pdfz/docunnents/2011/40699wang/ndx_wang.pdf.html (Year: 2011).*

(Continued)

*Primary Examiner* — Renee Robinson
(74) *Attorney, Agent, or Firm* — Bennett Jones LLP

(57) ABSTRACT

A method is provided for controlling bitumen recovery from an oil sands ore body in a bitumen extraction process by establishing and using a predictive ore processability model that accounts for multiple ore characteristics in planning ore deliveries from different locations of the ore body to produce a blended ore feedstock.

22 Claims, 19 Drawing Sheets

(51) Int. Cl.
*E21B 49/08* (2006.01)
*E21C 41/26* (2006.01)
*B03D 1/02* (2006.01)
*G01N 33/24* (2006.01)
*E21B 43/24* (2006.01)

(52) U.S. Cl.
CPC .......... *E21B 43/2406* (2013.01); *E21B 49/08* (2013.01); *E21C 41/31* (2013.01); *G01N 33/241* (2013.01)

(56) References Cited

U.S. PATENT DOCUMENTS

| | | | | |
|---|---|---|---|---|
| 2014/0347472 | A1* | 11/2014 | Davis | G01N 21/3563 |
| | | | | 348/135 |
| 2015/0299580 | A1* | 10/2015 | Moffett | B09B 3/0016 |
| | | | | 208/391 |
| 2017/0059544 | A1* | 3/2017 | Stafford | G01N 33/241 |

OTHER PUBLICATIONS

Sanford, "Processibility of Athabasca Oil Sand: Interrelationship Between Oil Sand Fine Solids, Process Aids, Mechanical Energy and Oil Sand Age after Mining", The Canadian Journal of Chemical Engineering, vol. 61, Aug. 1983, pp. 554-567 (Year: 1983).*
Clark, K. A. and D. S. Pasternack, "Hot Water Separation of Bitumen from Alberta Bituminous Sand", Industrial and Engineering Chemistry, vol. 24, No. 12, Dec. 1932, pp. 1410-1416 (Year: 1932).*
Liu, Jianjun et al, "Processability of Oil Sand Ores in Alberta", Energy & Fuels, Apr. 2005, 19, pp. 2056-2063 (Year: 2005).*
Nik, Leila Teymouri, "Development of an Enhanced Oil Sands Fluid Tailings Generation Model", Sep. 2016. (Year: 2016).*
"Surface Mining Techniques", Oil Sands Magazine, Jun. 2017, obtained from https://www.oilsandsmagazine.com/technical/mining/surface-mining on Feb. 4, 2020.*
"Mining for Bitumen", Oil Sands Magazine, Nov. 2017, obtained from https://www.oilsandsmagazine.com/technical/mining on Feb. 4, 2020.*

* cited by examiner

Table 1: Ore characteristics

| | |
|---|---|
| Depositional environment | Marine, Estuarine, Fluvial, Transition |
| Facies | Lithotype Code |
| Whole ore | Oil, water, solids content |
| Bitumen | viscosity |
| | Sulphur content |
| | Asphaltenes content |
| | Micro carbon residue |
| Solids | Organic Materials on Solids: amount of ash remaining (wt%) after all organic materials have been removed by sample ignition at 725 °C - loss on ignition (LOI) |
| | Particle Size Distribution: solids fractions (e.g., % < 1.9, 5.5, 44μm), $d_{10}$, $d_{50}$, $d_{90}$ in μm |
| | Element concentrations (ppm): Al, Ca, Fe, K, Mg, Na, Si, etc. |
| | Mineralogy: content of mineral species (wt%), including quartz, illite, kaolinite, etc. |
| | Methylene Blue Index in meq/100g |
| Connate water | pH |
| | Conductivity |
| | Element concentrations (mg/L): Ca, Fe, K, Mg, Na, Si, etc. |
| | Anion concentrations (mg/L): $F^-$, $Cl^-$, $NO_2^-$, $SO_4^{2-}$, $Br^-$, $NO_3^-$, $PO_4^{3-}$ |
| | Alkalinity: content of $CO_3^{2-}$ and $HCO_3^-$ (mg/L) |
| | Naphthenic acids content (mg/L) |

FIG. 3

Table 2

| Component | Analysis | Technique |
|---|---|---|
| Oil Sand | Oil, Water, Solids (O/W/S) | Dean Stark |
| Oil Sand - Bitumen | Sulphur Content<br>Asphaltenes Content<br>Micro Carbon Residue | ASTM D-5453<br>Pentane Insolubles<br>ASTM D-4530 |
| Oil Sand - Solids | Organic Materials on Solids<br>Particle Size Distribution<br>Solids Chemistry<br>Mineralogy<br>Methylene Blue Index | Loss in Ignition<br>Coulter Particle Analysis<br>Elemental Analysis of Solids<br>X-ray Diffraction<br>Methylene Blue |
| Oil Sand - Connate Water | Connate Water Chemistry using 0.1 micron filter | pH<br>Conductivity<br>Elemental Analysis of Water<br>Anions by Ion Chromatography<br>Alkalinity |

FIG. 4

| Ore Characteristic | | | Importance to Processability (A: High; B: Medium; C: Low) | Selection A: 9 parameters | Selection B: 5 parameters | Selection C: 12 parameters | Selection D: 30 parameters |
|---|---|---|---|---|---|---|---|
| Category | Parameter | Units | # | | | | |
| Core Sample Information | Mine | | | | | | |
| | Sample # | | | | | | |
| | Core ID | | | | | | |
| | Facies | | | | | | |
| | Depositional Environment | | | | | | |
| | Top Depth | m | | | | | |
| | Bottom Depth | m | | | | | |
| | Length | m | | | | | |
| Core Oil Sand Composition | Bitumen | % | 1 | A | Y | Y | Y |
| | Water | % | 2 | B | Y | Y | Y |
| | Solids | % | 3 | C | | | |
| Solids Particle Size Distribution (PSD) | <0.5µm | % | 4 | B | | | |
| | <1.9µm | % | 5 | A | Y | Y | Y |
| | <44µm | % | 6 | A | Y | Y | Y |
| | <125µm | % | 7 | C | | | |
| | >180µm | % | 8 | C | | | |
| | D50 | µm | 9 | B | Y | | Y |
| | D90 | µm | 10 | C | | | Y |

FIG. 5A

| Ore Characteristic | | | Importance to Processability (A: High; B: Medium; C: Low) | Selection A: 9 parameters | Selection B: 5 parameters | Selection C: 12 parameters | Selection D: 30 parameters |
|---|---|---|---|---|---|---|---|
| Solids Chemistry - Metal Element Content in Solids | Al | mg/kg | 11 | A | Y | | Y | Y |
| | Ba | mg/kg | 12 | C | | | | Y |
| | Ca | mg/kg | 13 | A | | | | Y |
| | Cd | mg/kg | 14 | C | | | | |
| | Co | mg/kg | 15 | C | | | | |
| | Cr | mg/kg | 16 | C | | | | |
| | Cu | mg/kg | 17 | C | | | | Y |
| | Fe | mg/kg | 18 | B | | | Y | Y |
| | K | mg/kg | 19 | B | | | | |
| | Mg | mg/kg | 20 | B | | | | |
| | Mn | mg/kg | 21 | C | | | | |
| | Na | mg/kg | 22 | B | | | | |
| | Ni | mg/kg | 23 | C | | | Y | Y |
| | P | mg/kg | 24 | C | | | | |
| | Si | mg/kg | 25 | B | | | Y | |
| | Sr | mg/kg | 26 | C | | | | |
| | Ti | mg/kg | 27 | C | | | | |
| | V | mg/kg | 28 | C | | | | |
| | Zn | mg/kg | 29 | C | | | | |
| | Zr | mg/kg | 30 | C | | | | |
| Solids Loss on Ignition | LOI | % Ash Remaining | 31 | A | | | | Y |

FIG. 5B

| Ore Characteristic | | | Importance to Processability (A: High; B: Medium; C: Low) | Selection A: 9 parameters | Selection B: 5 parameters | Selection C: 12 parameters | Selection D: 30 parameters |
|---|---|---|---|---|---|---|---|
| Solids Mineralogy XRD - Analysis | Quartz | % | 32 | A | | Y | Y |
| | Plagioclase Feldspar | % | 33 | C | | | |
| | Potassic Feldspar | % | 34 | C | | | |
| | Calcite | % | 35 | C | | | |
| | Dolomite | % | 36 | C | | | |
| | Anhydrite | % | 37 | C | | | |
| | Pyrite | % | 38 | B | | | |
| | Muscovite | % | 39 | C | | | |
| | Barite | % | 40 | C | | | |
| | Siderite | % | 41 | C | | | |
| | Kaolinite | % | 42 | A | | | Y |
| | Chlorite | % | 43 | C | | | |
| | Illite | % | 44 | A | | | Y |
| | Mixed-layer Clays | % | 45 | A | | | |
| | Smectite | % | 46 | A | | Y | Y |
| | Total Clay | % | 47 | A | | Y | Y |
| Solids Methylene Blue Index | MBI | meq/100g | 48 | A | Y | | Y |
| Solids Hydrophobicity | Average Critical Surface Tension | mN/m | 49 | A | | Y | Y |

FIG. 5C

| Ore Characteristic | | | Importance to Processability (A: High; B: Medium; C: Low) | Selection A: 9 parameters | Selection B: 5 parameters | Selection C: 12 parameters | Selection D: 30 parameters |
|---|---|---|---|---|---|---|---|
| Connate Water Chemistry | $CO_3^{2-}$ | 50 | mg/kg | B | | | | |
| | $HCO_3^-$ | 51 | mg/kg | B | | | | |
| | F | 52 | mg/kg | C | | | | |
| | Cl | 53 | mg/kg | A | | | Y | Y |
| | $NO_2^-$ | 54 | mg/kg | C | | | | |
| | $NO_3^-$ | 55 | mg/kg | C | | | | |
| | $PO_4^{3-}$ | 56 | mg/kg | C | | | | |
| | $SO_4^{2-}$ | 57 | mg/kg | A | | | | |
| | Br | 58 | mg/kg | C | | | | |
| | Al | 59 | mg/kg | C | | | | |
| | B | 60 | mg/kg | C | | | | |
| | Ba | 61 | mg/kg | C | | | | |
| | Ca | 62 | mg/kg | A | | | | Y |
| | Cd | 63 | mg/kg | C | | | | |
| | Co | 64 | mg/kg | C | | | | |
| | Cr | 65 | mg/kg | C | | | | |
| | Cu | 66 | mg/kg | C | | | | |
| | Fe | 67 | mg/kg | A | | | | Y |
| | K | 68 | mg/kg | A | | | | Y |
| | Li | 69 | mg/kg | C | | | | |
| | Mg | 70 | mg/kg | C | | | | Y |

FIG. 5D

| Ore Characteristic | | | Importance to Processability (A: High; B: Medium; C: Low) | Selection A: 9 parameters | Selection B: 5 parameters | Selection C: 12 parameters | Selection D: 30 parameters |
|---|---|---|---|---|---|---|---|
| Connate Water Chemistry (continued) | Mn | mg/kg | 71 | C | | | | |
| | Mo | mg/kg | 72 | C | | | | Y |
| | Na | mg/kg | 73 | A | | | Y | |
| | Ni | mg/kg | 74 | C | | | | |
| | P | mg/kg | 75 | C | | | | |
| | Pb | mg/kg | 76 | C | | | | |
| | S | mg/kg | 77 | C | | | | |
| | Sb | mg/kg | 78 | C | | | | |
| | Se | mg/kg | 79 | A | | | | Y |
| | Si | mg/kg | 80 | C | | | | |
| | Sr | mg/kg | 81 | C | | | | |
| | Ti | mg/kg | 82 | C | | | | |
| | V | mg/kg | 83 | C | | | | |
| | Zn | mg/kg | 84 | C | | | | |
| | Zr | mg/kg | 85 | C | | | | |
| | Divalents | mg/kg | 86 | A | Y | | Y | |
| | Mono-valents | mg/kg | 87 | A | Y | | | |
| | Surfactants content | mg/kg | 88 | A | | | Y | Y |
| | pH | | 89 | A | Y | | Y | Y |
| | Conductivity | mS/cm | 90 | A | | | Y | Y |
| Bitumen Characteristics | Sulphur content | mg/kg | 91 | B | | | | Y |
| | nitrogen content | mg/kg | 92 | C | | | | |
| | Asphaltene | % | 93 | B | | | Y | Y |
| | Microcarbon Residue | % | 94 | C | | | | Y |

FIG. 5E

CONTROLLING BITUMEN RECOVERY FROM AN OIL SANDS ORE BODY BY USING A PREDICTIVE ORE PROCESSABILITY MODEL IN PRODUCING A BLENDED ORE FEEDSTOCK

FIELD OF THE INVENTION

The present invention relates to a method for controlling bitumen recovery from an oil sands ore body in a bitumen extraction process by establishing and using a predictive ore processability model that accounts for multiple ore characteristics in planning ore deliveries from different locations of the ore body to produce a blended ore feedstock.

BACKGROUND OF THE INVENTION

Oil sands ore is a mixture of bitumen, minerals including clays and sands, and water. Recovering bitumen from the ore begins with excavating the ore, such as by using a shovel in an open pit mine. Trucks deliver the excavated ore in discrete deliveries to a hopper, which in turn feeds the ore to a crusher. The crushed ore is mixed with water and steam to form a slurry. A pipeline hydro-transports the slurry to an extraction facility where it is subjected to gravity separation in a primary separation vessel (PSV) to produce a bitumen froth process stream and a tailings stream. The bitumen froth is further treated with light hydrocarbon solvent and subjected to mechanical separation processes to recover bitumen.

The quality of ore used to make the slurry affects bitumen recovery at the extraction facility. For example, in comparison to ores having high grade (i.e., bitumen content of about 10 to 12 percent or higher) and low fines content (i.e., less than about 20 percent), ores that have low grade (i.e., bitumen content of about 6 to 10 percent) and high fines content (greater than about 30 percent) tend to be associated with lower bitumen recovery to the froth, and greater bitumen loss to the tailings. The challenge of maintaining a desired bitumen recovery rate at the extraction facility is compounded by variations in ore quality throughout the ore body, and potentially, limited amounts of high grade, low fines ore.

In order to produce an oil sands ore feedstock of relatively constant composition for the extraction facility, ores of different qualities may be roughly blended when producing the slurry. Current ore blending practices attempt to control only two ore characteristics in the ore blend: ore grade (bitumen content) and fines content (i.e. the content of solid particles having a diameter less than 44 microns). These characteristics are used to control bitumen extraction process parameters such as caustic dosage, and water addition. Feed rate of the slurry may also be varied based on production requirements, and in response to excursions in bitumen recovery observed at the extraction facility.

However, current ore blending practices are not always satisfactory. Despite controlling ore grade and fines content within acceptable ranges, actual bitumen recovery may vary significantly from expected recovery. This may be due to the effect of numerous other ore characteristics, and their interaction with each other, that are important or even critical to bitumen recovery. Moreover, current ore blending practices are not based on predicted bitumen recovery, and make it difficult to identify causes of poor ore processability and appropriate coping strategies.

The planned delivery sequence of ores to the hopper can also be upset by equipment breakdown and downtime, and limited capacity of the surge piles at the hopper. These upsets may be undiagnosed until several hours later when an increase in bitumen loss to the tailings is noticed at the extraction facility. By then, however, it is too late to take remedial action in respect to either ore blending at the hopper, or process control at the extraction facility that would positively impact the material already being processed at the extraction facility.

Accordingly, there is a need in the art for improvements to ore blending practices with a view to controlling bitumen recovery from ore bodies in bitumen extraction processes.

SUMMARY OF THE INVENTION

In one aspect, the present invention provides a method for controlling bitumen recovery from an oil sands ore body in a bitumen extraction process, the method comprising the steps of:
(a) obtaining core samples from a plurality of spatially separated locations within the ore body;
(b) performing characterization tests on the core samples to establish a first database of sets of ore characteristic values comprising a bitumen content, and one or a combination of:
 (i) a water content;
 (ii) a solids content;
 (iii) a percentile solids particle size;
 (iv) a content of solid particles having a diameter less than 1.9 microns;
 (v) a content of ore formed in a marine depositional environment;
 (vi) a metal element content, wherein the metal element comprises one or a combination of: aluminium, barium, calcium, cadmium, cobalt, chromium, copper, iron, potassium, magnesium, manganese, sodium, nickel, phosphorus, silicon, strontium, titanium, vanadium, zinc, and zirconium;
 (vii) a solids loss on ignition parameter measured as a percentage of ash remaining after heating of the core samples;
 (viii) a mineral content, wherein the mineral comprises one or a combination of: quartz, plagioclase feldspar, potassic feldspar, calcite, dolomite, anhydrite, pyrite, muscovite, barite, siderite, kaolinite, chlorite, illite, mixed-layer clays, smectite, and total clay;
 (ix) a methylene blue index;
 (x) a solids hydrophobicity parameter comprising an average critical surface tension;
 (xi) a connate water chemistry parameter comprising, in respect to the connate water in the core samples, one or a combination of: carbonate ion content, hydrogencarbonate ion content, fluoride ion content, chloride ion content, nitrite ion content, nitrate ion content, phosphate ion content, sulfate ion content, bromide ion content, aluminium content, boron content, barium content, calcium content, cadmium content, cobalt content, chromium content, copper content, iron content, potassium content, lithium content, magnesium content, manganese content, molybdenum content, sodium content, nickel content, phosphorus content, lead content, sulphur content, antimony content, selenium content, silicon content, strontium content, titanium content, vanadium content, zinc content, zirconium content, a divalent cation content, a monovalent cation content, a surfactant content, a pH level, and an electrolytic conductivity;

(xii) a bitumen parameter, comprising in respect to the bitumen in the core samples, one or a combination of: sulphur content, nitrogen content, asphaltene content, and microcarbon residue;

(c) performing processability tests on the core samples to establish a second database of processability values indicative of any one or a combination of bitumen recovery from ore in the core samples in the bitumen extraction process, a bitumen content of bitumen froth in the bitumen extraction process, a solids content of bitumen froth in the bitumen extraction process, and a water content of bitumen froth in the bitumen extraction process, and (d) based on the first and second databases, determining a predictive ore processability model for predicting processability values from a specified set of ore characteristic values.

In one embodiment of the method, the sets of ore characteristic values comprise the combination of the bitumen content, and the water content.

In one embodiment of the method, the sets of ore characteristic values comprise the combination of the bitumen content, and the 50th percentile solids particle size.

In one embodiment of the method, the sets of ore characteristic values comprise the combination of the bitumen content, and the aluminum content.

In one embodiment of the method, the sets of ore characteristic values comprise the combination of the bitumen content, and the pH level of the connate water.

In one embodiment of the method, the sets of ore characteristic values comprise the combination of the bitumen content, a content of solid particles having a diameter less than 44 microns, and the content of ore formed in a marine depositional environment.

In one embodiment of the method, the sets of ore characteristic values comprise the combination of the bitumen content, a content of solid particles having a diameter less than 44 microns, the water content, the 50th percentile solids particle size, the aluminium content, the methylene blue index, the divalent cation content of the connate water, the monovalent cation content of the connate water, and the pH level of the connate water.

In one embodiment of the method, the sets of ore characteristic values comprise the combination of the bitumen content, the content of solid particles having a diameter less than 1.9 microns, a content of solid particles having a diameter less than 44 microns, and the 50th percentile solids particle size.

In one embodiment of the method, the sets of ore characteristic values comprise the combination of the bitumen content, the content of solid particles having a diameter less than 1.9 microns, the aluminium content, the quartz content, the total clay content, the average critical surface tension, the chloride ion content in the connate water, the sodium content in the connate water, the divalent ions content in the connate water, the pH level of the connate water, the electrolytic conductivity of the connate water, and the asphaltene content of the bitumen.

In one embodiment of the method, the sets of ore characteristic values comprise the combination of the bitumen content, the content of solid particles having a diameter less than 1.9 microns, a content of solid particles having a diameter less than 44 microns, the 50th percentile solids particle size, the aluminium content, the calcium content, the iron content, the magnesium content, the silicon content, the percentage of ash remaining after heating of the core samples, the quartz content, the kaolinite content, the illite content, the total clay content, the methylene blue index, the average critical surface tension, the chloride ion content in the connate water, the calcium content in the connate water, the iron content in the connate water, the potassium content in the connate water, the magnesium content in the connate water, the sodium content in the connate water, the silicon content in the connate water, the surfactant content in the connate water, the pH level of the connate water, the electrolytic conductivity of the connate water, the sulphur content of the bitumen, the asphaltene content of the bitumen, and the microcarbon residue of the bitumen.

In one embodiment of the method, the processability values are indicative of bitumen recovery from ore in the core samples in the bitumen extraction process.

In one embodiment of the method, the processability values are indicative of the bitumen content of bitumen froth in the bitumen extraction process.

In one embodiment of the method, the processability values are indicative of the solids content of bitumen froth in the bitumen extraction process.

In one embodiment of the method, the processability values are indicative of the water content of bitumen froth in the bitumen extraction process.

In one embodiment of the method, the predictive ore processability model comprises a rule correlating a range of ore characteristic values with a range of processability values. The rule may be determined by using a computer implementing a pattern recognition algorithm.

In one embodiment of the method, the method further comprises the steps of:

(a) incorporating the predictive ore processability model in a geologic block model of the ore body describing the ore characteristic values at block locations, to predict processability values for ore at the block locations; and (b) using the predicted processability values for ore at the block locations in determining planned amounts of ore deliveries from the block locations to a feed location of the bitumen extraction process within a time interval to produce a planned ore blend having a predicted bitumen recovery value within a predetermined range.

In one embodiment of the method described immediately above, the method may further comprise the step of:

(a) based on the planned amounts, allocating mining equipment to the block locations to deliver ore from the block locations to a feed location to produce a blended ore feedstock for the bitumen extraction process.

In one embodiment of the method described immediately above, the method may further comprise the steps of:

(a) generating delivery records for ore deliveries to the feed location of the bitumen extraction process, within the time interval, wherein the delivery records comprise:
  (i) information indicative of block locations from which the ore deliveries originated; and
  (ii) actual amounts of the ore deliveries;

(b) using a computer, generating a graphical user interface comprising:
  (i) a graphical representation of the planned amounts of ore deliveries from the block locations to the feed location within the time interval; and
  (ii) a graphical representation of the actual amounts of ore deliveries from the block locations to the feed location within the time interval, based on the delivery records.

In one embodiment of the method described immediately above, the method may further comprise the steps of:

(a) generating a bitumen extraction process record for an actual amount of bitumen recovered or lost from the feedstock; and
(b) using the computer, generating the graphical user interface further comprising:
  (i) a graphical representation of the actual amount of bitumen recovered or loss from the feedstock, based on the bitumen extraction process record.

In one embodiment of the method, the method further comprises the step of determining, based on the predictive ore processability model, an ore blending rule for the ore body that prescribes a combination of the ore characteristic values to achieve either a desired bitumen recovery or a desired bitumen froth quality, or both a desired bitumen recovery and a desired bitumen froth quality, from ore in the ore body in the bitumen extraction process.

In one embodiment of the method, the method further comprises the step of:
(a) incorporating the ore characteristic values in a geologic block model of the ore body to describe the ore characteristic values at block locations;
(b) generating delivery records for ore deliveries to a feed location of the bitumen extraction process, within a time interval, wherein the delivery records comprise:
  (i) information indicative of block locations from which the ore deliveries originated; and
  (ii) actual amounts of the ore deliveries;
(c) based on the delivery records and the geologic block model of the ore body, determining a set of ore characteristic values for a blended ore feedstock produced by the ore deliveries to the feed location within the time interval; and
(d) based on the predictive ore processability model, predicting the processability value for the determined set of ore characteristic values for the blended ore feedstock.

In one embodiment of the method described immediately above, the method further comprises the step of:
(a) based on the predicted processability value for the determined set of the ore characteristic values for the blended ore feedstock, varying an operational parameter of the bitumen extraction process.

BRIEF DESCRIPTION OF THE DRAWINGS

In the drawings shown in the specification, like elements may be assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention.

FIG. 3 shows Table 1 summarizing examples of ore characteristics of core samples that may be used to determine a predictive ore processability model.

FIG. 4 shows Table 2 summarizing examples of characterization tests that may be performed on core samples to determine certain ore characteristics.

FIGS. 5A to 5E show a Table summarizing additional examples of ore characteristics of core samples, and subcombinations thereof, which may be used to determine a predictive ore processability model.

DETAILED DESCRIPTION OF PREFERRED EMBODIMENT

Definitions.

Any term or expression not expressly defined herein shall have its commonly accepted definition understood by a person skilled in the art. As used herein, the following terms have the following meanings.

"Oil sands ore" refers to a mixture of bitumen, minerals, and water prior to being subjected to a bitumen extraction process.

"Grade" refers to the bituminous component of an oil sands ore.

"Fines" refers to the solids component an oil sands ore having a particle diameter less than 44 microns.

"Marine" refers to the component of an oil sands ore formed in a marine depositional environment.

"Bitumen extraction process" refers to a process in which a slurry comprising bitumen, solids and water, is subjected to conditioning in a hyrdrotransport pipeline and gravity separation in a primary separation vessel (PSV) to produce a bitumen froth as the product.

"Bitumen froth" refers to a mixture of bitumen, water, and solids that is recovered in a bitumen extraction process.

"Percentile solids particle size" refers to the particle diameter corresponding to a percentile rank in a cumulative particle size distribution of solid particles in an oil sands ore. For example, $d_{50}$, refers to the particle diameter corresponding to a $50^{th}$ percentile rank in a cumulative particle size distribution of solid particles in an oil sands ore.

"Computer processor", "computer", "computer device", and "computer workstation" and like terms refer to one or more electronic devices capable of performing operations on data. Non-limiting examples of processors and computers include devices referred to as servers, general purpose computers, personal computers, desktop computers, laptop computers, handheld computers, microprocessors, tablets, telephones, mobile phones, smart phones, and the like. A processor or computer may comprise a single physical device, or multiple physical devices operatively connected to each other (e.g., a network of computers).

"Computer readable medium" or "CRM" refers to a non-transitory, tangible medium capable of persistently encoding information in a format readable by a computer processor. Non-limiting examples of CRM include magnetic media (e.g., a magnetic diskette or tape), optical media (e.g., an optical disc), and solid-state media using integrated circuits (e.g., flash memory).

"Communications network" refers to a network enabling electronic communications between computer processors. In embodiments, a communication network may comprise one or a combination of the Internet, a local area network, and a telephone network (whether wired or wireless.

Method Overview.

Figure 1:
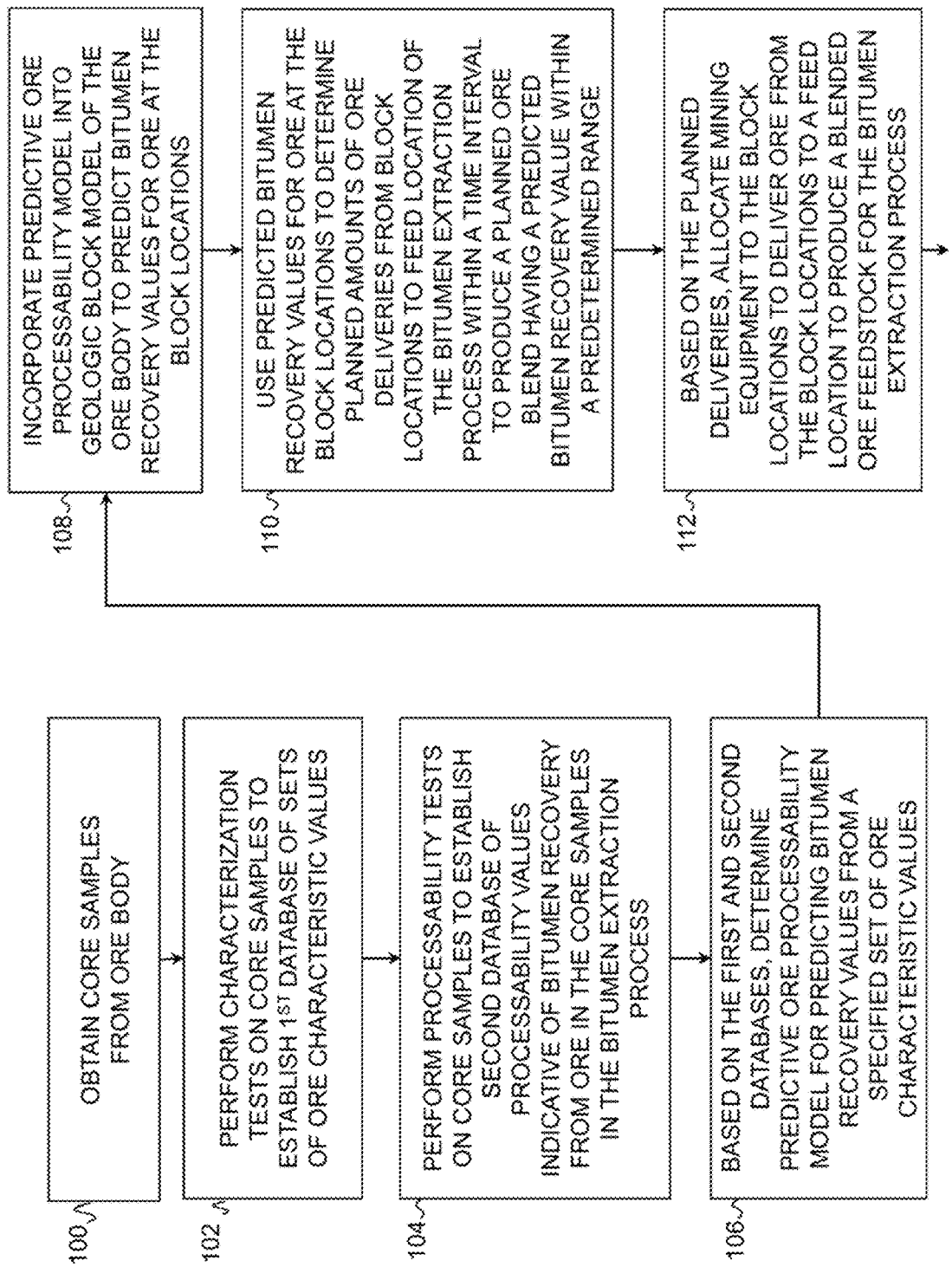
FIGS. 1 and 2 show a flow chart of an embodiment of a method of the present invention.
Figure 2:
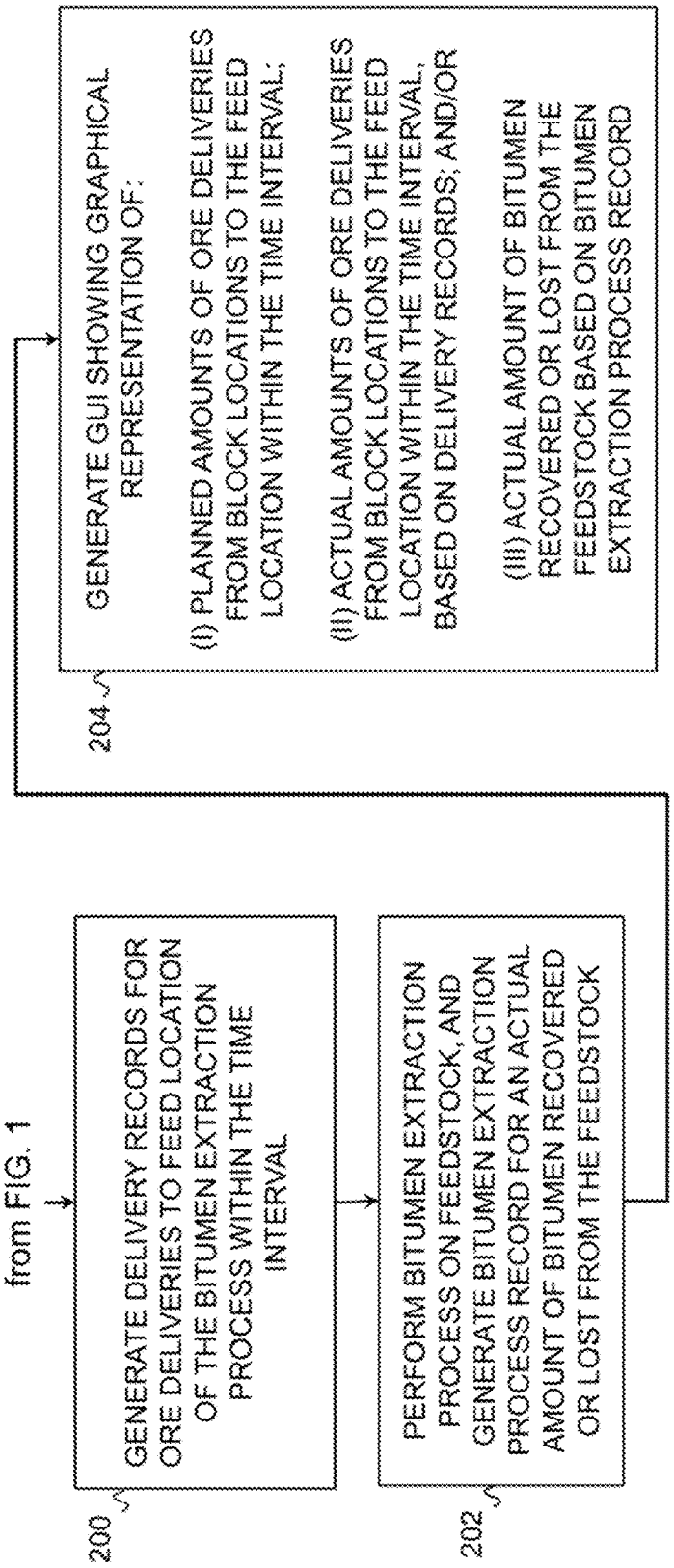

FIGS. 1 and 2 show a flow chart of an embodiment of a method of the present invention, the steps of which are described in greater detail below.

Core Sample Collection.

The method begins by obtaining core samples from a plurality of spatially separated locations within an ore body (step 100). When the core samples are obtained, they should be associated with a location within the ore body (e.g., as described by geographical coordinates and an elevation from the surface) so that the ore characteristic values and processability values determined in subsequent steps of the method can be incorporated into a geologic block model of the ore body. The number of core samples obtained may vary with factors such as the size of the ore body and the expected variation in ore characteristics throughout the ore body. However, a greater number of core samples will generally allow for the determination of a more robust predictive ore processability model in subsequent steps of the method. As a non-limiting example, the method may involve collecting cores at dozens to hundreds of locations of the ore body, with each core extending over numerous elevations, to produce hundreds or thousands of core samples.

Characterization Tests.

The method continues by performing characterization tests on the core samples to establish a first database of sets of ore characteristic values (step 102). The set of ore characteristic values includes the bitumen content, the fines content, and at least one or combination of additional ore characteristics as shown in Table 1 of FIG. 3. In a preferred embodiment, the set of ore characteristics includes the combination of a bitumen content, a water content, a solids content, a fines content, a percentile solids particle size (e.g. $d_{50}$ or $d_{90}$), a methylene blue index, an aluminum content, a pH level of connate water, and a content of monovalent and divalent cations (e.g., sodium, potassium, calcium, magnesium) in connate water. The inventors have found that these ore characteristics are influential in the processability of oil sands ore. In one study, use of these ore characteristics allowed determination of a predictive ore processability model having an accuracy of about 80 percent. The characterization tests that are used will depend on the ore characteristics to be determined. Exemplary techniques that may be used for the characterization tests for certain ore characteristics are summarized in Table 2 of FIG. 4.

In other embodiments, the set of ore characteristics may reflect additional or alternative physical or chemical properties of the ore, which may be relevant to the efficacy of bitumen recovery in the bitumen extraction process. For example, FIGS. 5A to 5E show a Table summarizing ninety-four (94) examples of ore characteristic values that may be used to determine a predictive ore processability model. The inventors have assigned a rank of "A", "B", or "C" to the importance of each characteristic to ore processability, to denote characteristics believed to have high, medium, and low importance, respectively. FIGS. 5A to 5E also show examples of sub-combinations of the characteristics that may be used in the predictive ore processability model. The sub-combination of selection "A" includes 9 characteristics, all of which are of either medium or high importance. The sub-combination of selection "B" includes 5 characteristics consisting of bitumen content, water content and three particle size distribution characteristics. The sub-combination of selection "C" includes 12 characteristics, including at least one characteristic from each of the major categories of ore characteristics. The most comprehensive sub-combination of selection "D" includes 30 characteristics, including at least one characteristic from each of the major categories of ore characteristics. As a further non-limiting example, the combination of ore characteristic values that may be used to determine the predictive ore processability values may include the combination of the bitumen content, a content of solid particles having a diameter less than 44 microns, and an ore formed in a marine depositional environment—i.e., a combination of "grade", "fines" and "marine".

Processability Tests.

The method continues by performing processability tests on the core samples to establish a second database of processability values indicative of bitumen recovery from the core samples in the bitumen extraction process (step 104). As an example, the processability tests may involve processing the core samples in a reduced-scale testing facility that simulates processing of the ore sample in a bitumen extraction process at a full scale extraction facility. The processability value may be expressed as a weight percentage of the bitumen in the froth over the total bitumen in the core sample, which is generally referred to as bitumen recovery.

In addition, the processability tests on the core samples can also establish processability values that are indicative of the quality of the bitumen froth produced from the bitumen extraction process. The quality of the froth may be expressed as the contents of the three primary components (bitumen, water, and solids) in the froth, or as the ratios of bitumen to water and bitumen to solids. It is typically expected that the extraction process can produce a froth that contains at least 60 wt % bitumen, less than 30 wt % water, and less than 10 wt % solids. In terms of ore processability, both bitumen recovery and froth quality are important and should be considered for modelling.

Predictive Ore Processability Model.

At the conclusion of steps 102 and 104, the method results in a first database of sets of ore characteristic values, and a second database of processability values. The method continues by using the first and second databases to determine a predictive ore processability model for predicting processability values from a specified set of ore characteristic values (step 106).

The predictive ore processability model can be determined by a variety of mathematical techniques operating on the first and second databases. For example, in embodiments, the predictive ore processability model may be determined by statistical techniques (e.g., principal component analysis, or multiple regression) operating on the first and second databases. These methods may be accurate where it can be validly assumed that the relationship between the ore characteristics and the bitumen recovery is accurately modelled by a particular mathematical relationship, that the effect of a particular ore characteristic on bitumen recovery is independent of the effect of other ore characteristics, and that core samples have ore characteristics within an expected range without outliers. In practice, however, one or more of these assumption may not be valid.

Accordingly, in other embodiments, the model may be determined by machine learning techniques such as neural networks, or pattern recognition of high-order associations between multiple ore characteristic values and processability values in the databases. As understood by persons of ordinary skill in the art of machine learning, pattern recognition involves using a computer to implement algorithms to identify reasonable, if not exact, relationships between inputs (e.g., the sets of ore characteristics in the first database) and outputs (e.g., the processability values in the second database). Such methods may be implemented with the assistance of software tools (e.g., Association Discovery™ of the Discovery*e™ analytical engine; Pattern Discovery Technologies, Waterloo, Ontario). While the mathematics underlying the determination of the predictive ore processability model may be complicated, the following example illustrates the premise by which a predictive ore processability model may be determined in respect to a single ore characteristic—namely, the amount of fines (particles having a diameter less than 44 µm). It will be understood that the method can be applied to other ore characteristics, and extended to combinations of multiple ore characteristics.

Figure 6:
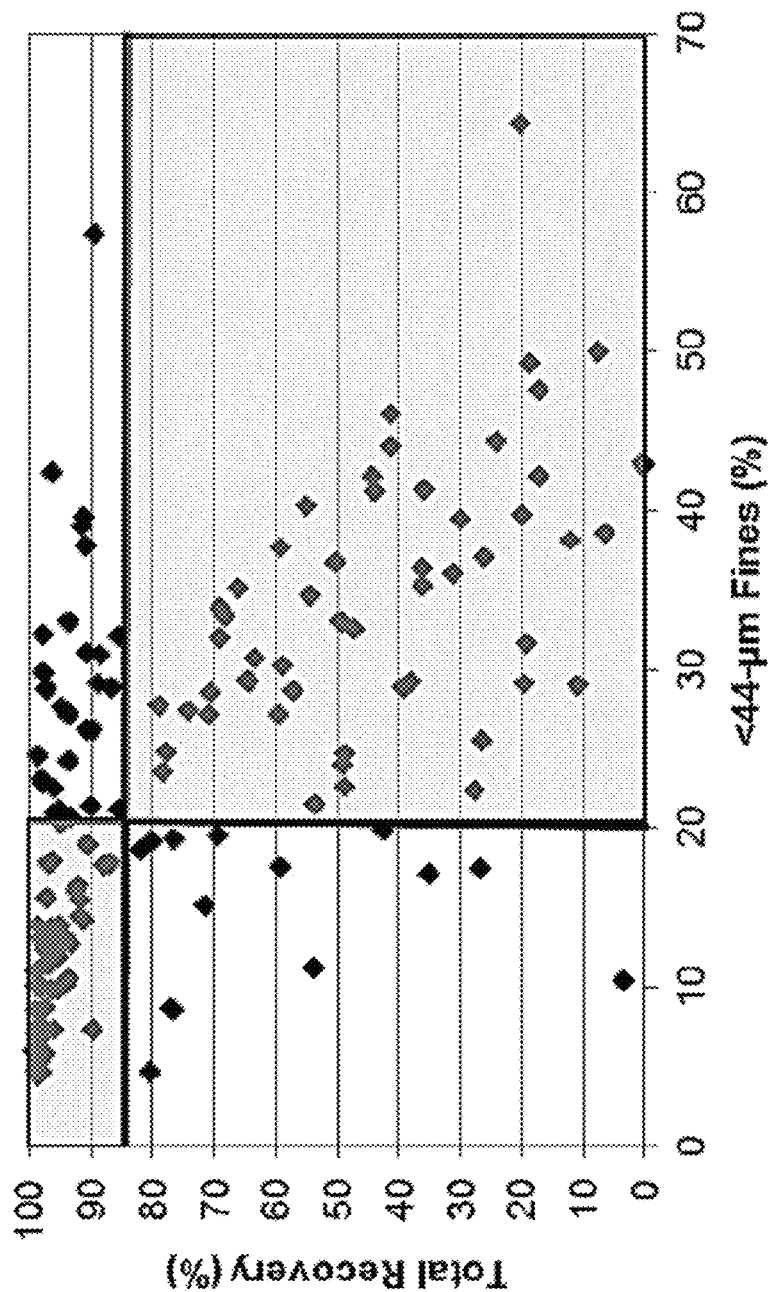
FIG. 6 is a chart showing an example of coincidence between fines content, and total bitumen recovery, for numerous cores samples of an ore body.

In this example, FIG. 6 is a plot of 149 ore records, showing the coincidence between the amount of fines in the ore, and the total bitumen recovery. In this example: (i) 64 of the samples contained less than 20% fines; (ii) 85 contained in excess of 20% fines; (iii) 69 of the samples yielded less than 85% total recovery; and (iv) 80 yielded greater than 85% total recovery. Each of these four conditions is called a discrete event.

Probability calculations can be used to determine the theoretical frequency of combined events (e.g., <10% bitumen and >85% recovery), given the frequencies of discrete events and assuming that the events are independent of each other. A joint expected probabilistic distribution of frequencies where various combinations of events coincide can be established under this assumption. Joint expected probabilities exist given the discrete events that characterized the records: <20% fines and <85% total recovery—30 records; <20 fines and >85% total recovery—34 records; >20% fines and <85% total recovery—39 records; and >20% fines and >85% total recovery—46 records.

The actual occurrences of the joint events can be obtained from the first and second databases, and compared to the expected values from the distribution, assuming independence among events that were calculated above. The actual joint events, in the same order as described above were 14, 50, 55 and 30 records. The white areas in FIG. 6 identify joint events that occurred less often than anticipated (i.e., the joint event of low fines and low recovery and the joint event of high fines and high recovery). Conversely, the other two joint events identified by the gray shading occurred more often than anticipated. The statistical significance of these patterns can be calculated.

While a pattern of joint events depicts the significance of the relationship among the discrete events, it does not provide a prediction. In order to add predictive capability to the discovered patterns, a joint event pattern is transformed into a rule in the form similar to "IF fines content is <20%, THEN total recovery is >85%". The strength of this rule is measured by the information gain when total recovery is >85% on the condition the input ore has <20% fines. This is an example of a positive rule. The information gain or Weight of Evidence (WOE) is positive. (WOE measures the difference of the information provided by input condition (A) in support of the output being (B) and the support of the output being not (B). WOE is a descriptor of the strength of a rule that is significant at a given confidence level relative to other rules that are significant at the same confidence level.) Negative rules occur when the information gain or WOE is negative. A negative rule implies that a defined output is not likely to happen given a defined input. An example of a negative rule from FIG. 6 would be "IF fines content is <20%, THEN total recovery is not likely to be <85%".

One can determine, by way of WOE, when a certain input is observed, which output is more likely to happen. For example, given an input of ore with <20% fines, one would be more confident predicting the recovery in the >85% range than in the <85% range, if the WOE of the rule "IF fines <20%, THEN recovery >85%" is positive while the WOE of the rule "IF fines <20%, THEN recovery <85%" is negative or has a much smaller positive value.

Using the above approach, the predictive ore processability model can be determined as a database of a plurality of "IF, THEN" type rules. The collection of rules, each with its own WOE, represents the predictive ore processability model for predicting the most likely range of total bitumen recovery for an oil sand ore having a specified set of ore characteristic values.

Incorporation of Predictive Ore Processability Model in Geologic Block Model.

As known to persons of ordinary skill in the art of geological modelling, a geologic block model represents an ore body with a plurality of spatially discrete 3-dimensional regions or "block locations", each of which is associated with geological variables such as the sets of the ore characteristic values. A geologic block model may be implemented with the assistance of software tools (e.g., SURPAC™; Dassault Systèmes, Vélizy-Villacoublay, France). After the predictive ore processability model has been determined, the method continues by incorporating the predictive ore processability model in a geologic block model of the ore body describing the ore characteristic values at block locations, to predict processability values for ore at the block locations (step 108).

Figure 7:
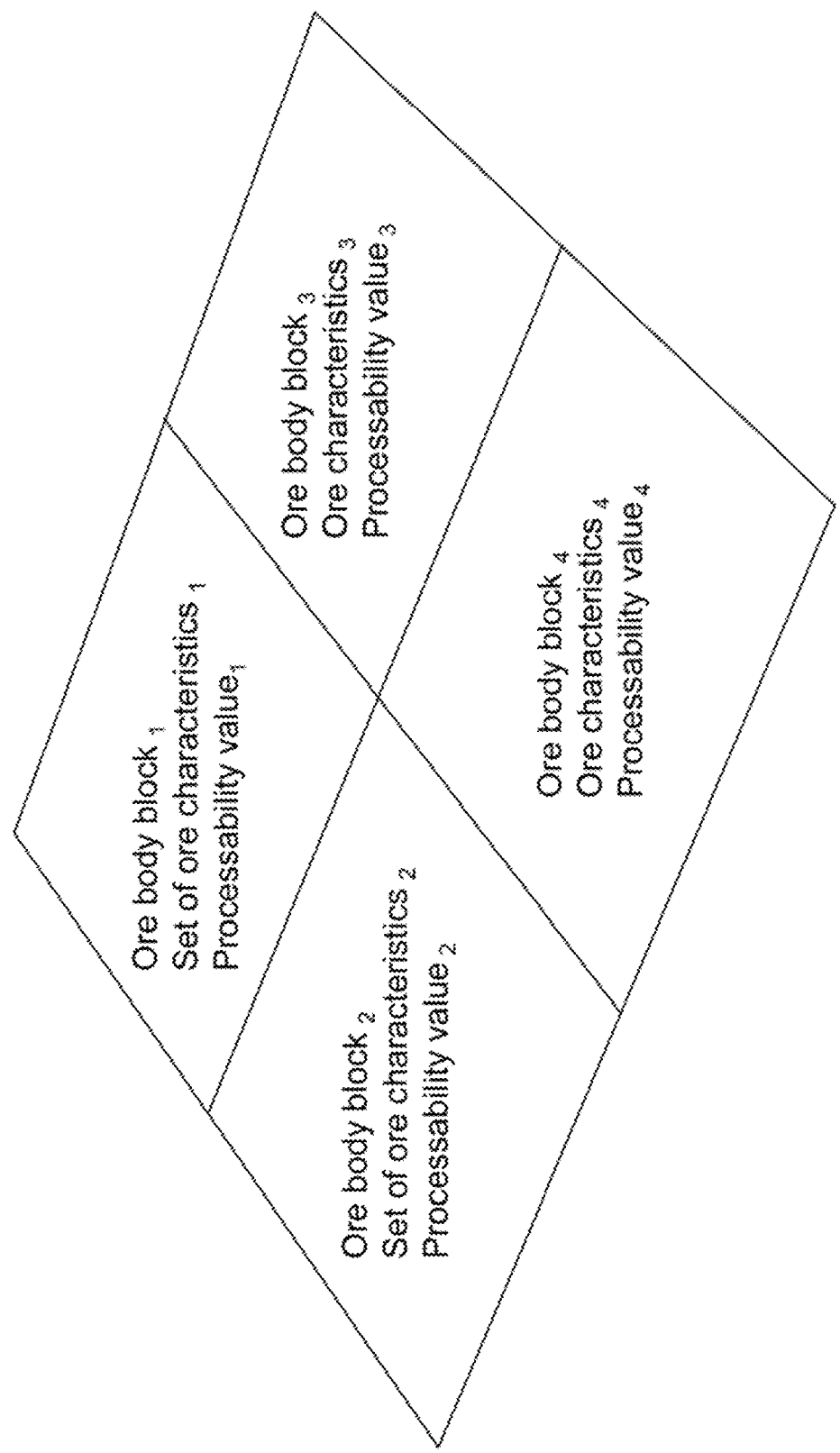
FIG. 7 is a simplified representation of a geologic block model with processability values predicted by a predictive ore processability model.

The resulting geologic block model effectively provides a three-dimensional map of the sets of ore characteristic values and predicted processability values for the ore in different block locations of the ore body. For example, FIG. 7 is a conceptual map of the sets of ore characteristic values and processability values in four block locations of an ore body arranged in a 2×2 array. It will be appreciated that the map shown in FIG. 7 is highly simplified in comparison to geologic block model used in practice, which may describe several thousand block locations in three-dimensional space. Each one of the block locations may be distinguished by a location identifier that uniquely identifies the block location from other block locations in the ore body. For example, each ore body block location may be identified by a coordinate system, or a naming convention.

Mine Planning.

Figure 8:
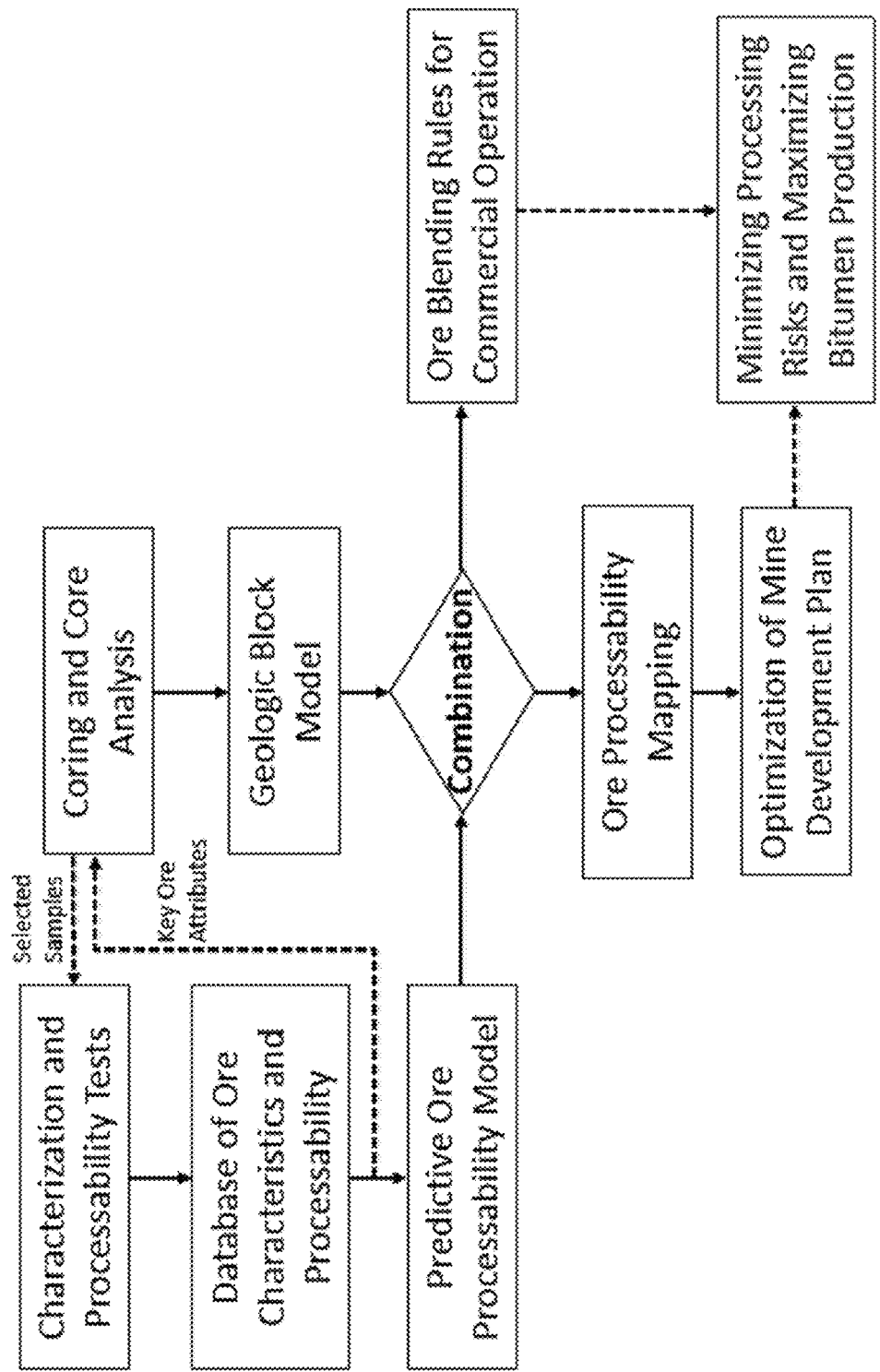
FIG. 8 is a functional diagram showing the development of a predictive ore processability model and its use with a geologic block model in long-range mine planning operations.

Once the predictive ore processability model has been incorporated into the geologic block model, it may be used for a variety of mine planning purposes. The mine planning may be long-range in nature in the sense of relating to relative large block locations, and considering the planned use of the ore body from a life cycle perspective. FIG. 8, for example, shows the development of a predictive ore processability model and its use with a geologic block model in long-range mine planning operations, to develop ore processability maps, or developing ore blending rules, all with a view to maximizing bitumen production from the ore body (and/or maximizing bitumen froth quality by increased bitumen content and lower solids and water content in the bitumen froth) while minimizing processing risk.

Figure 9:
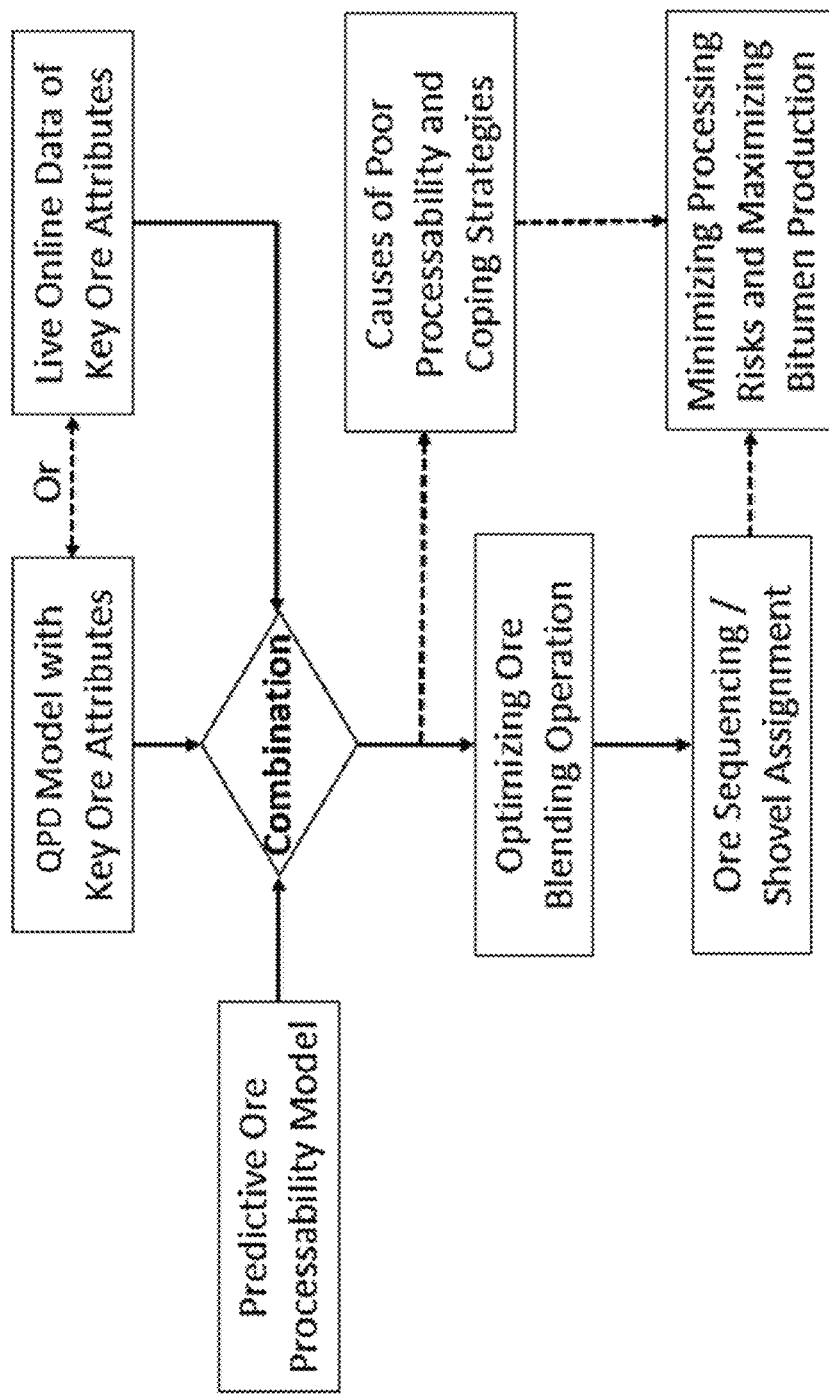
FIG. 9 is a functional diagram showing the use of a predictive ore processability model with a quality production data (QPD) model of key ore attributes in short-range mine planning operations.

Alternatively, or additionally, the geologic block model may be used for short-range mine planning or production scheduling to guide the mining process within relatively short time frames, such as a daily basis, a shift-to-shift basis, or even an hourly basis. FIG. 9, for example, is a functional diagram showing the use of a predictive ore processability model with a quality production data (QPD) model in short-range mine planning operations, to optimize ore blending operations, ore sequencing at the level of shovels and trucks at the mine site, to diagnose problems of poor processability, again all with a view to maximizing bitumen production from the ore body (and/or maximizing bitumen froth quality by increased bitumen content and lower solids and water content in the bitumen froth) while minimizing processing risk (e.g., unforeseen upsets at the bitumen extraction facility).

In one embodiment, the method continues by using the predicted processability values for ore at the block locations in determining planned amounts of ore deliveries from the block locations to a feed location of the bitumen extraction process within a time interval to produce a planned ore blend having a predicted bitumen recovery value within a predetermined range (step 110). As an example of use of the geologic block model in short-range daily mine planning, the incorporated predictive ore processability model is used to optimize ore blending, based on the resulting ore characteristic values of a blended ore feedstock produced from ores delivered from different locations within the ore body to a feed location where the deliveries are mixed. For instance, in order to achieve an ore blend with predicted ore processability value, shovels may be allocated to different locations within the ore body, based on ore processability model, known information regarding the productivity of the shovels, and known information about delivery times from the different locations to a feed location of the bitumen extraction process.

The predicted processability values may be used in a variety of ways in determining planned amounts of ore deliveries from the block locations. For example, optimization algorithms may select block locations having processability values that attempt to maximize predicted bitumen recovery, or keep the predicted bitumen recovery within acceptable ranges. The implementation of such algorithms may be semi-automated or fully-automated by computer implementation.

Alternatively, the predictive ore processability model could be used to develop ore blending rules that prescribe combinations of ore characteristic values to achieve a desired bitumen recovery. The determination of such a rule may be implemented using an optimization algorithm that determines the combination of ore characteristic values that maximize predicted bitumen recovery, or keep predicted bitumen recovery within acceptable ranges. The implementation of such algorithms may be semi-automated or fully-automated by computer implementation.

Ore Delivery.

The method continues with allocating mining equipment to the block locations to deliver ore from the block locations to a feed location to produce a blended ore feedstock for the bitumen extraction process, based on the planned amounts (step 112). For example, the planned amounts of ore deliveries determined in step 110, may be used to assign excavating equipment (e.g., shovels and trucks) to particular block locations of the ore body with a view to achieving the planned amounts of ore deliveries. These assignments may be made having regard to factors such as the excavation rates of shovels, the haul capacity of the trucks, and cycle times of the trucks between block locations and the feed location.

Operational Data Collection, Analysis, and Visualization.

Ideally, the actual amounts of ore delivered from each of the block locations should match the planned amounts of ore, within acceptable tolerances. In practice, however, the actual amounts and planned amounts may deviate from each other due to variation in operating practices or unforeseen events (e.g., equipment breakdown and downtime), with consequential effects on the bitumen recovery at the extraction facility. The ability to track and compare actual ore deliveries to the feed location, and bitumen recovery at the bitumen extraction facility would be beneficial to operators in managing operations both at the mine site and at the bitumen extraction facility. Further, the ability to relate this information back to the predictive model, and the geological block model, may provide valuable insights for diagnosing causes of poor processability, and determining appropriate coping strategies.

Accordingly, in one embodiment, the method continues with generating delivery records for ore deliveries to the feed location of the bitumen extraction process, within the time interval (step 200). The delivery records include information indicative of block locations from which the ore deliveries originated, and actual amounts (e.g., weight or volume) of the ore deliveries. In one embodiment, the method also continues with generating a bitumen extraction process record for an actual amount of bitumen recovered or lost from the feedstock (step 202). A computer may then be used to generate a graphical user interface (GUI) that displays graphical representations of one or more of: planned amounts of ore deliveries from the block locations to the feed location within the time interval; actual amounts of ore deliveries from the block locations to the feed location within the time interval, based on the delivery records; and the actual amount of bitumen recovered or loss from the feedstock, based on the bitumen extraction process record.

First Example

Figure 10:
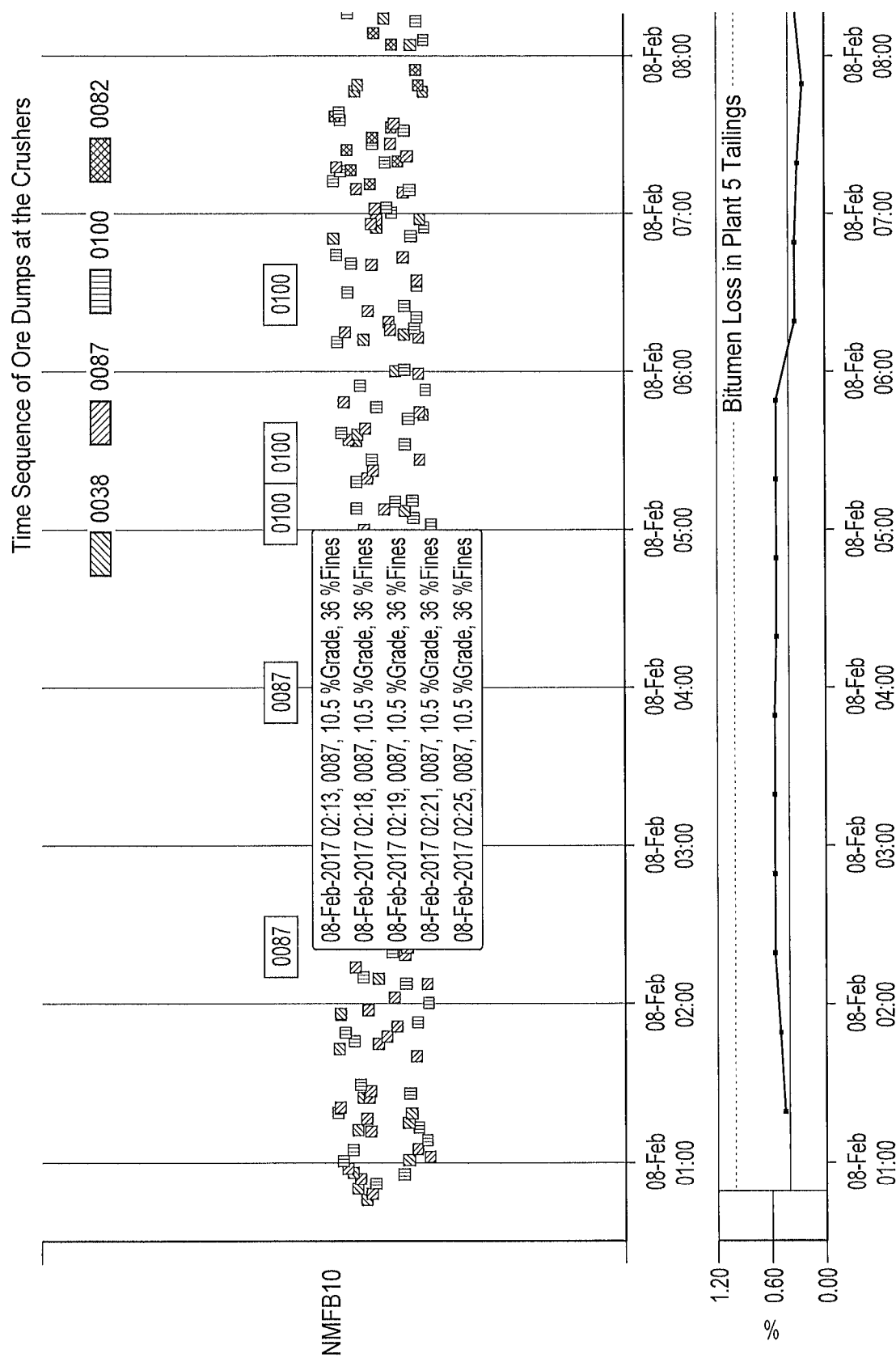
FIG. 10 is an embodiment of a GUI showing a time series of ore deliveries from different shovels to a hopper and crusher assembly, and a time series of bitumen loss in tailings of a PSV.

FIG. 10 shows a graphical representation of a time series based on deliver records, and a time series based on a retrieved bitumen extraction process record. Of note, the two graphical representations are disposed vertically adjacent each other and have a common horizontal time scale to facilitate correlation between them.

The graphical representation of the delivery records is a chart having a plurality of markers. Each one of the markers corresponds to a single delivery of ore to a feed location of the bitumen extraction process, and has a position measured along the horizontal axis of the chart based on the time of delivery to the feed location (e.g., a hopper and crusher assembly). Each one of the markers has an applied color-coding based on a mining equipment unit identifier (e.g. shovel ID "0038", "0087", "0100" or "0082") associated with the mining equipment unit that excavated the ore in the delivery. (The mining equipment identifier may be determined through association of the location identifier in the delivery record with the mine plan that allocates one of the shovels to one of the block locations of the ore body). Therefore, in the illustrated examples, the shovel ID serves as a proxy for the block location.) In other embodiments, the markers may have additional or alternative applied visual coding schemes to differentiate the markers based on the mining equipment unit identifier, such as a color scale, a pattern, a texture, or a symbol.

In embodiments, each one of the markers corresponding to one of the deliveries is selectable via the GUI to retrieve and display, on the GUI, values of the delivery record for one of the deliveries. For example, one or more of the markers may be selectable by a pointing device such as a computer mouse to position a cursor in proximity of one of the markers, "hovering" the cursor over the one or more markers, and/or depressing a button of the computer mouse to "click" on the one or more markers. In FIG. 10, for example, a cluster of five markers within a delivery time range of 02:13 to 02:25 have been selected. Upon their selection, a "popup tooltip" appears to display the delivery times, shovel IDs, grade content, and fines content of the deliveries corresponding to the markers.

In embodiments, the GUI may include input controls (e.g., text boxes, selectable radio buttons, drop-down lists, check buttons, etc.) that allow a user to input or select filtering criteria that control the display of markers. As an example, a preset radio button may be selected to display only markers corresponding to deliveries associated with a specific one of the shovel IDs or ore body block location. As another example, a preset radio button may be selected to display only markers corresponding to a delivery sequence having a pattern of associated shovel IDs or ore body block location. For instance, the display may show only those sets of markers corresponding to a number (e.g., three or five) of consecutive deliveries associated with the same shovel ID or block location to detect a delivery sequence that may result in suboptimal blending of different ores at the feed location.

The graphical representation of a time series of the bitumen extraction process record is a line chart having a plurality of markers. Each one of the markers corresponds to a particular process time. Each one of the markers has a position measured along the horizontal axis of the chart based on the one of the process times. Each one of the markers has a position measured along the vertical axis of the chart based on a value of the rate of bitumen loss to the tailings, at one of the process times.

Second Example

Figure 11:
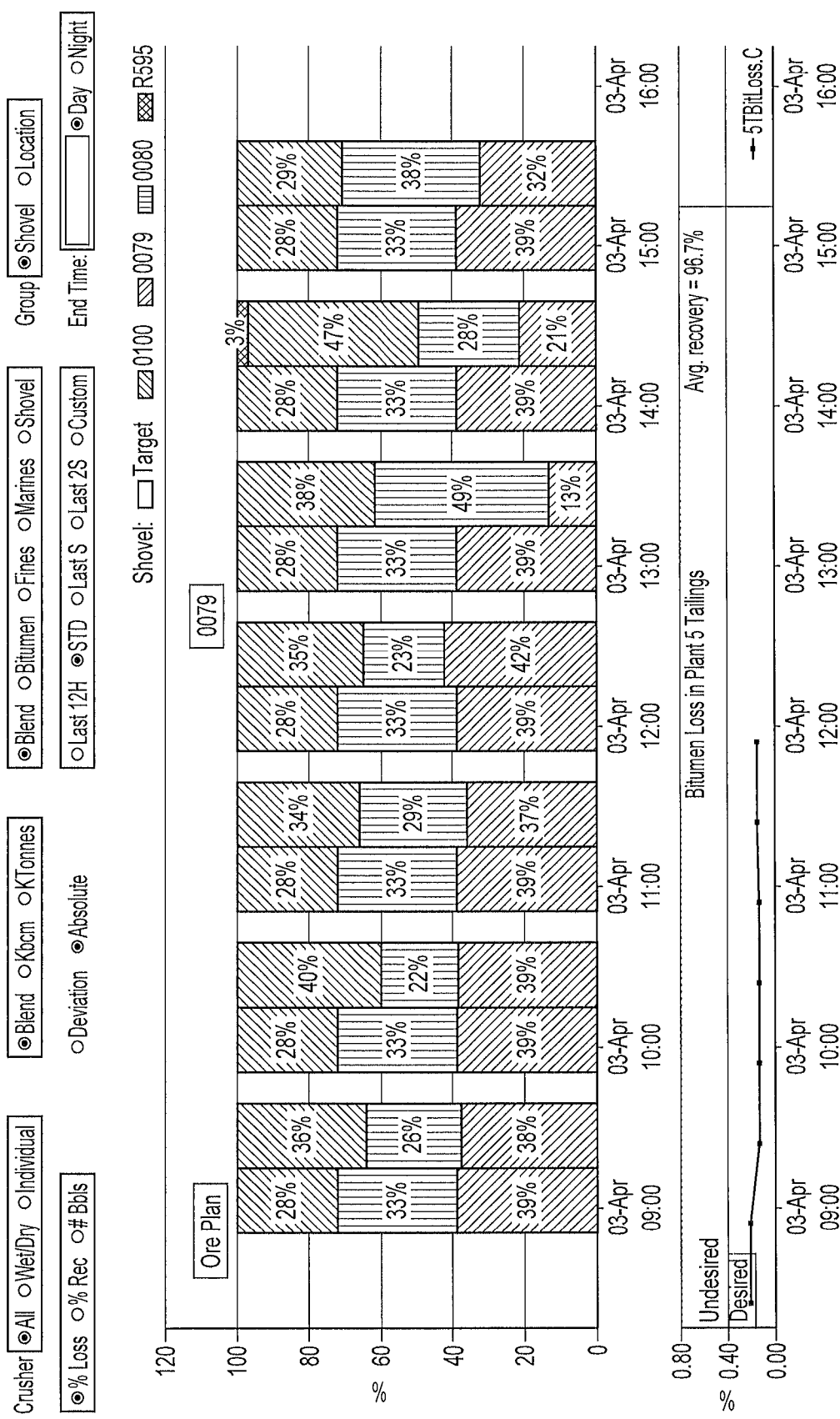
FIG. 11 is an embodiment of a GUI showing a time series of actual and planned ore deliveries from different shovels to a hopper and crusher assembly, and a time series of bitumen loss in tailings of a PSV.

FIG. 11 shows a graphical representation of a time series of a first feedstock parameter in the form of stacked bar charts (actual and planned), a time series of a second feedstock parameter (actual and planned) in the form of values and/or a line graph superimposed on the stacked bar charts, and a time series based on the bitumen extraction process record in the form of a line graph. Again, the graphical representations of the first and second feedstock parameters are disposed vertically adjacent the graphical representation of the process record to facilitate correlation between them.

Figure 12:
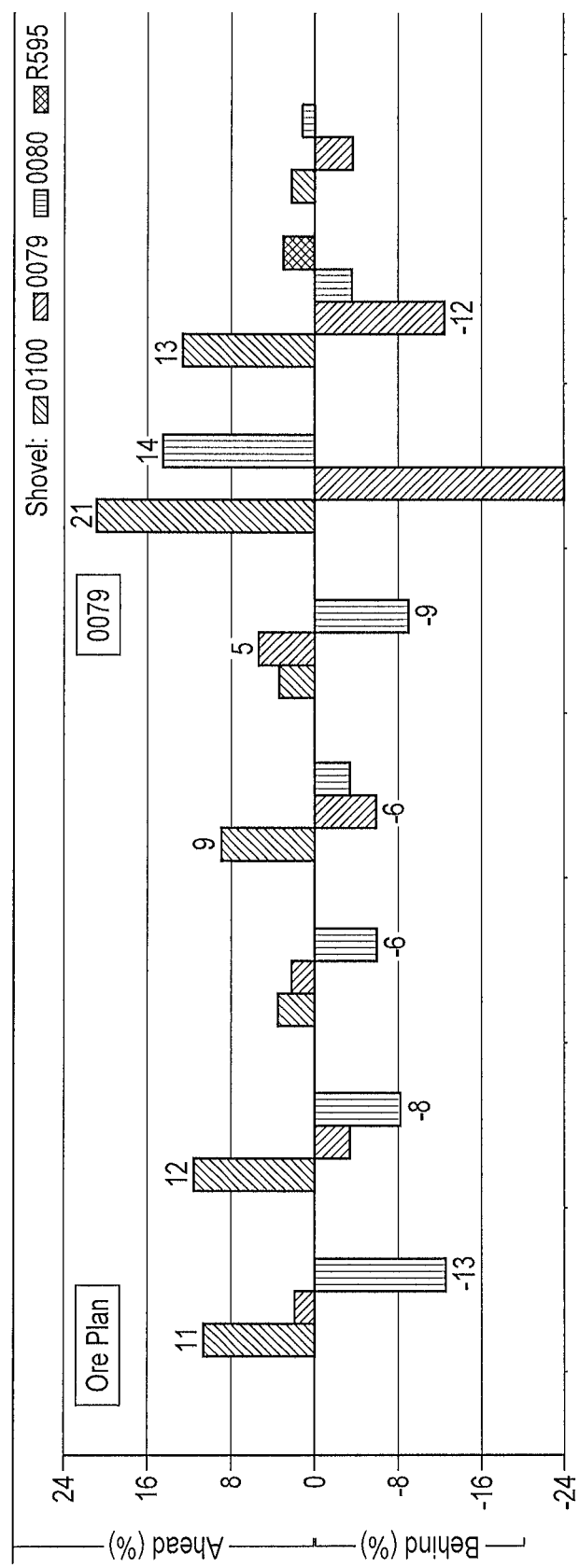
FIG. 12 is an embodiment of a GUI showing a chart of a time series of deviation between actual and planned ore deliveries from different shovels to a hopper and crusher assembly at different time periods.
Figure 13:
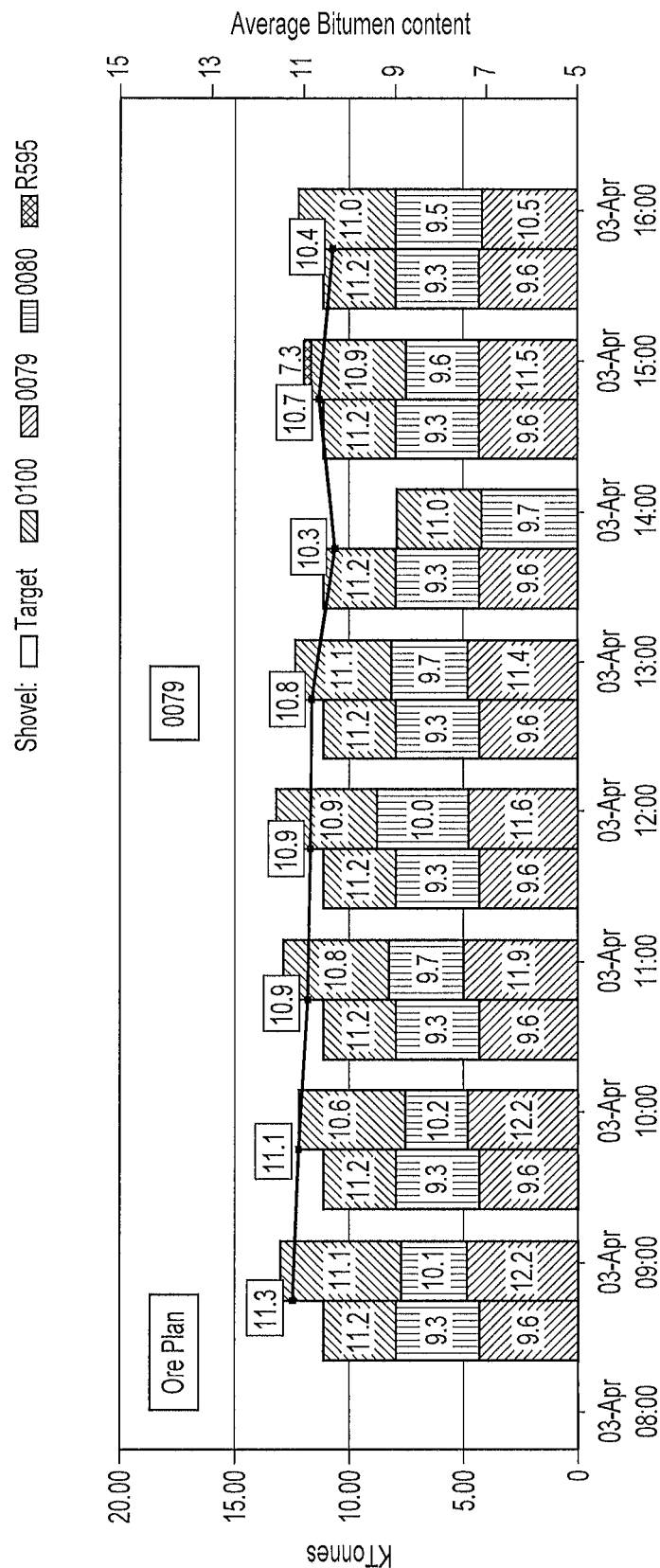
FIG. 13 is an embodiment of a GUI showing a chart of a time series of actual and planned ore deliveries by different shovels, and a time series of actual and planned weighted averages of bitumen content of ore deliveries from different shovels to a hopper and crusher assembly, and for the feedstock as a whole.
Figure 14:
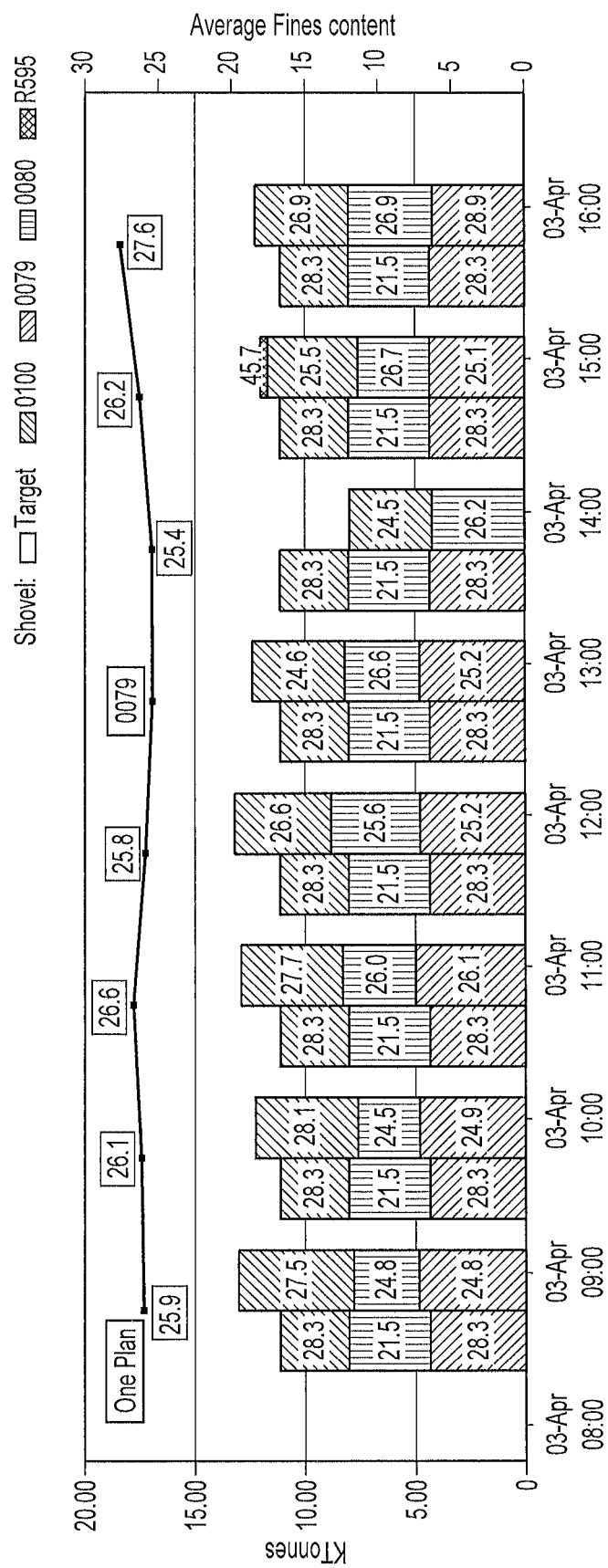
FIG. 14 is an embodiment of a GUI generated by the system of the present invention, including a chart of a time series of actual and planned weight of ore deliveries from different shovels, and a time series of actual and planned weighted averages of fines content of deliveries from different shovels to a hopper and crusher assembly at different time periods, and for the feedstock as a whole.

The GUI shown in FIG. 11 has several groups of radio buttons located near the top of the display, which are selectable by a user to produce alternative graphical representations of the first and second feedstock parameters as shown in FIGS. 12 to 14.

The group of radio buttons labelled "Shovel" and "Location" are selectable by the user to show the data either based on shovel IDs, or based on block locations, which can be related to the shovel IDs through the mine planning record.

The group of radio buttons labelled "All", "Wet/Dry" and "Individual" are selectable by the user to display data for different crushers, where present.

The group of radio buttons labelled "% Loss", "% Rec" and "# Bbls" are selectable by the user to show the time series of bitumen extraction process data at the bottom of FIG. 11 in different modes. Selection of "% Loss" shows the bitumen extraction process data as a rate of bitumen loss to tailings, as shown in FIG. 11. Selection of "% Rec" shows the process data as a rate of bitumen recovery from the bitumen extraction process. Selection of "# Bbls" shows the bitumen loss as an absolute volume measured in barrels.

The group of radio buttons labelled "Last 12H", "STD", "Last S", Last 2S", and "Custom" are selectable by the user to define the range of time periods shown. "Last 12H" refers to the immediately preceding 12 hour period, "STD" refers to the "shift-to-date", "Last S" refers to the last shift, "Last 2S" refers to the last two shifts", and "Custom" refers to a customizable time range.

The group of radio buttons labelled "blend %", "Kbcm" and "KTonnes" are selectable by the user to display a first feedstock parameter (actual and planned) in the form of stacked bar charts within a time interval. The time interval is preferably sufficiently long to include several deliveries to the feed location, but not so long as to aggregate deliveries that would not be expected to be blended together at the feed location. In the embodiment shown in FIG. 11, the duration of the time interval is one hour. In other embodiments, the time interval may have a different duration such as a half-hour.

The radio button labelled "blend %" selects the first feedstock parameter by the weight-based blend fraction of feedstock contributed by each of the mining unit equipment identifiers during each of the one-hour periods. For example, suppose that: there are that there are k shovel IDs (j=1, . . . k); each shovel ID, j, is associated with n truck deliveries (i=1, . . . n) during a time period of one hour (the value of n may be different for each shovel ID); and each truck delivery, i, sourced from the $j^{th}$ shovel ID is associated with a weight of ore of $m_{j,i}$ (tonnes). The weight-based blend fraction of feedstock contributed by the $j^{th}$ shovel ID, $F_j$, can be determined as follows:

$$F_j = \frac{\sum_{i=1}^{i=n} m_{j,i}}{\sum_{j=1}^{j=k} \sum_{i=1}^{i=n} m_{j,i}}$$

The radio button labelled "Kbcm" selects the display of actual and planned volumes of feedstock contributed by each of the mining unit equipment identifiers during each of the one-hour periods. For example, suppose that: there are that there are k shovel IDs (j=1, ... k); each shovel ID, j, is associated with n truck deliveries (i=1, ... n) during a time period of one hour (the value of n may be different for each shovel ID); and each truck delivery, i, sourced from the $j^{th}$ shovel ID is associated with a volume of ore of $v_{j,i}$ (Kbcm). The volume of feedstock contributed by the $j^{th}$ shovel ID, $V_j$ can be determined as follows:

$$V_j = \sum_{i=1}^{i=n} v_{j,i}$$

The radio button labelled "KTonnes" selects the display of actual and planned weight of feedstock contributed by each of the mining unit equipment identifiers during each of the one-hour periods. For example, suppose that: there are that there are k shovel IDs (j=1, ... k); each shovel ID, j, is associated with n truck deliveries (i=1, ... n) during a time period of one hour (the value of n may be different for each shovel ID); and each truck delivery, i, sourced from the $j^{th}$ shovel ID is associated with a weight of ore of $m_{j,i}$ (tonnes). The volume of feedstock contributed by the $j^{th}$ shovel ID, $M_j$, can be determined as follows:

$$M_j = \sum_{i=1}^{i=n} m_{j,i}$$

The group of radio buttons labelled "Deviation" and "Absolute" are selectable by the user to select the mode in which the stacked bar charts for the planned and actual first feedstock parameter are displayed. The radio button labelled "absolute" selects the display of bars for the planned and absolute values adjacent to each other for each of the time periods. The radio button labelled "Deviation" selects the display of a single bar corresponding to the difference in value between the actual and planned values for each of the time periods.

The group of radio buttons labelled "blend %", "Kbcm" and "KTonnes" are selectable by the user to display a second feedstock parameter (actual and planned) in the form of values and/or a line graph superimposed on the stacked bar charts representing the first feedstock parameter.

The radio button labelled "blend" selects the second feedstock parameter to be the weight-based blend fraction of feedstock contributed by each of the mining unit equipment identifiers during each of the one-hour periods. (This is determined in the same manner as discussed above for the radio button "blend %" for the first feedstock parameter.)

The radio buttons labelled "Bitumen" (synonymous with "grade" (g)), "Fines", and "Marine" selects the second feedstock parameter be the weight-averaged bitumen, fines and marine content of feedstock contributed by each of the mining unit equipment identifiers during each of the one-hour periods. For example, suppose that: there are that there are k shovel IDs (j=1, ... k); each shovel ID, j, is associated with n truck deliveries (i=1, ... n) during a time period of one hour (the value of n may be different for each shovel ID); and each truck delivery, i, sourced from the $j^{th}$ shovel ID is associated with a weight of ore of $m_{j,i}$ (tonnes), a grade content of $g_{j,i}$ (%), a fine content of $f_{j,i}$ (%), and a marine content of $r_{j,i}$ (%). The weight-averaged grade content $g_j$, fines content $f_j$, and marine content $r_j$, contributed by the $j^{th}$ shovel ID, can be determined as follows:

$$g_j = \frac{\sum_{i=1}^{i=n} g_{j,i} m_{j,i}}{\sum_{i=1}^{i=n} m_{j,i}}$$

$$f_j = \frac{\sum_{i=1}^{i=n} f_{j,i} m_{j,i}}{\sum_{i=1}^{i=n} m_{j,i}}$$

$$r_j = \frac{\sum_{i=1}^{i=n} r_{j,i} m_{j,i}}{\sum_{i=1}^{i=n} m_{j,i}}$$

Having regard to the foregoing display options, FIG. 11 shows the GUI when the "Shovel", "Blend %", "Blend" and "Absolute" radio buttons are selected. Of note, the stacked bar chart shows the planned ("target") blend fraction (left) adjacent to the actual blend fraction (right), contributed by each of the shovels ("0100", "0079", "0080", "R595") for each of the one hour time periods. Further, the numerical values of the planned and actual blend fraction contributed by each shovel are shown superimposed on the stacked segment of the bar corresponding to the shovel.

Third Example

FIG. 12 shows a GUI with the same selected options as for the GUI of FIG. 11, except that the "Deviation" radio button has been selected in preference to the "Absolute" radio button. Accordingly, in contrast to FIG. 11, the stacked bar chart shows a single bar having a dimension based on the difference in values between the actual and planned blend fractions contributed by each of the shovels, for each of the time periods.

Fourth Example

FIG. 13 shows a GUI with the same selected options as for the GUI of FIG. 10, except that the "KTonnes" radio button has been selected in preference to the "% Blend" radio button, and that the "Bitumen" radio button has been selected in preference to the "Blend" radio button. Accordingly, in contrast to FIG. 11, the stacked bar chart shows planned and actual values of weight of ore contributed by each of the shovels, for each of the one hour time periods. Further, the GUI shows numerical values of the planned and actual weight-averaged bitumen content of deliveries contributed by each shovel for each time period, superimposed on the stacked segment of the bar corresponding to the shovel. Further still, the GUI shows a line chart and numerical values (in boxes adjacent markers of the line chart) for the weight-averaged bitumen content of deliveries contributed by all shovels for each time period.

Fifth Example

FIG. 14 shows a GUI with the same selected options as for the GUI of FIG. 11, except that that the "Fines" radio button has been selected in preference to the "Bitumen" radio button. Accordingly, in contrast to FIG. 11, the GUI shows numerical values of the planned and actual weight-averaged fines content of deliveries contributed by each shovel for each time period superimposed on the stacked segment of the bar corresponding to the shovel. Further still, the GUI shows a line chart and numerical values (in boxes adjacent markers of the line chart) for the weight-averaged fines content of deliveries contributed by all shovels for each time period.

Process Optimization.

The predictive ore processability model may further be used to predict the processability of a blended ore feedstock, resulting from actual deliveries of ore from different block locations within the ore body to the feed location of the bitumen extraction process. For instance, as described above, the timing of actual deliveries of ore from different locations of the ore body to a feed location may be monitored and recorded. This information may be used to determine the ore characteristics of the resulting blended ore feedstock at the feed location. The predictive ore processability model may then be used on the determined set of ore characteristics of the blended ore feedstock, to predict the processability of the blended ore feedstock. This predicted processability can then be used as a basis for adjusting operational parameters of the bitumen extraction process, with a view to optimizing or controlling bitumen froth quality (i.e., the bitumen content or the solids content or the water content of the bitumen froth) and bitumen recovery from bitumen extraction process.

Computer Implementation in an Integrated Oil Sands Process.

Figure 15:
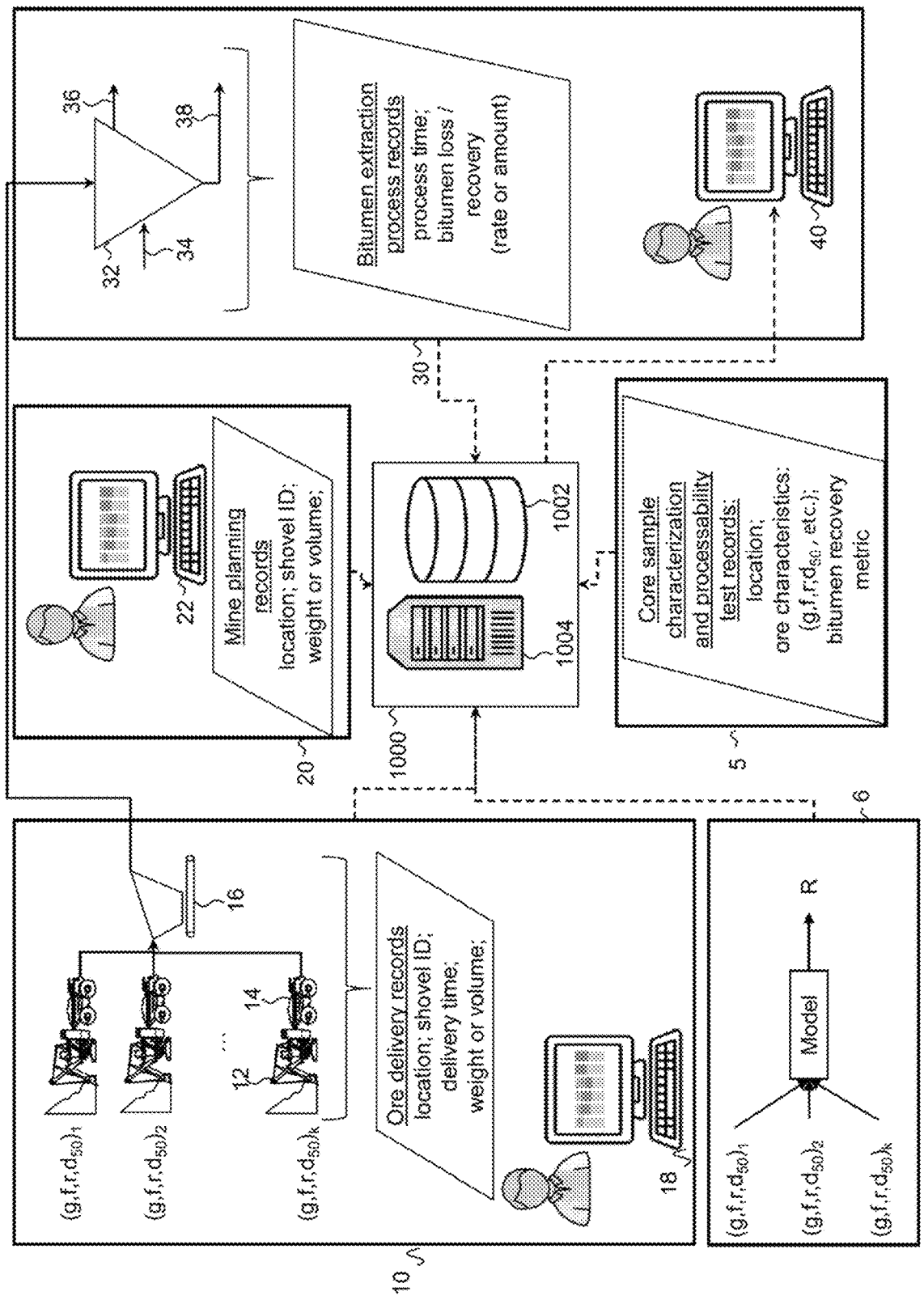
FIG. 15 is a schematic illustration of an embodiment of a computer system of the present invention that integrates ore mine excavating operations, mine planning operations, and extraction facility operations in a process for extracting bitumen from oil sands ore.

FIG. 15 shows a schematic illustration of an embodiment of a computer system (1000) of the present invention in relation to oil sands ore mine excavating operations (10), mine planning operations (20), and extraction facility operations (30) in a process for extracting bitumen from oil sands ore.

Mine Excavating Operations.

The mine excavating operations (10) involve mining equipment units (12) that excavate oil sand ore from geological deposits. In the embodiment shown in FIG. 15, the mining equipment units (12) are a plurality of shovels (1 through k), but in other embodiments may comprise additional or alternative types of excavation equipment. Each of the shovels excavates oil sands ore from one of the block locations of the ore body.

The mine excavating operations (10) involve delivery of discrete deliveries of oil sands ore excavated by each of the mining equipment units to a feed location of the bitumen extraction process, where the deliveries are roughly blended together. In the embodiment of FIG. 15, the deliveries are delivered by trucks (14) that travel routes between the shovels and the feed location (16) comprising a hopper and crusher assembly, which mixes the ore and discharges it to a mixing device that mixes the ore with water and steam to produce a slurry that is hydro-transported by pipeline to the extraction facility. In other embodiments, the deliveries may be delivered by additional or alternative types of vehicles to a feed location comprising additional or alternative types of ore processing equipment.

The mine excavating operations (10) generate the aforementioned delivery records. In the embodiment shown in FIG. 15, these ore delivery records include:
   an identifier indicative of the block location from which the one of the deliveries originated;
   a mining equipment identifier that identifies the one of the mining equipment units that excavated the one the deliveries (e.g., an alpha-numeric shovel ID such as "0100", "0079", "0080" or "R595");
   a delivery time of the one of the deliveries to the feed location (e.g., a date and time of arrival at the hopper and crusher assembly); and
   an amount of ore in the delivery (e.g., a weight/mass of ore measured in tonnes (1000 kg) and/or volume of ore measured in trillions of cubic meters (kbcm)).

The system is not limited by any particular manner by which the delivery parameters are determined and acquired. As a non-limiting example, the delivery time to the feed location of the one of the deliveries may be determined by analyzing a combination of time-logging and GPS-tracking data of trucks as they cycle between one of the shovels, and the hopper and crusher assembly. The mining equipment identifiers may be assigned according to naming protocols of the mine site operator. The weight of ore in the delivery may be determined by weigh scales that weigh the trucks delivering the deliveries to the hopper and crusher assembly. The volume of ore in the delivery may be determined based on the weight of the ore in the delivery and an estimated density of the ore, or using volume measuring instruments.

Of note, each of the delivery records includes an identifier indicative of the block location from which the one of the deliveries originated. Likewise, each of the core sample records (5) includes a location identifier that uniquely distinguishes the block location from other block locations. Therefore, by cross-referencing the block location identifier in a particular delivery record with the corresponding block location identifier in one of the core sample records, the particular delivery record can be associated with the set of ore characteristics.

The mine excavating operations may be associated with a mine site computer workstation (18) under control of a mine site operator such as dispatcher of the trucks. The mine site computer workstation (18) includes a display device (e.g., a computer monitor), and interacts with the system (1000) to generate on the display device a GUI, as described above.

Mine Planning Operations.

The mine planning operations (20) involve generation of mine planning records for operation of mine site equipment at the mine site to produce the deliveries of ore. In the embodiment shown in FIG. 15, the mine planning records may include the following information for each one of the block locations:
   a planned amount (e.g., a weight or volume) of ore to be delivered to the feed location from each of the block locations of the ore body; and
   a planned delivery time to the feed location of the delivery (e.g., a date and time of arrival at the hopper and crusher assembly).

As a non-limiting example, the planned amount of ore to the feed location may be determined by operator knowledge of the estimated amount of feedstock needed to recover an expected amount of bitumen, having regard to estimated recovery efficiencies. The planned delivery time to the feed location of the planned contribution may be determined based on the planned contribution and operator knowledge of flow rate of a slurry comprising the ore through the PSV. Alternatively, the above data may be determined using the predictive ore processability model, as described above.

The mine planning operations may be associated with a planning computer workstation (22) under control of a plan operator responsible for generating the planned feedstock parameters. The planning computer workstation (22) includes a display device (e.g., a computer monitor), and interacts with the system (1000) to generate on the display device a GUI, as is described above.

Extraction Facility Operations.

The extraction facility operations (30) involve using process equipment for extracting bitumen from the feedstock produced from the oil sands ore. In the embodiment shown in FIG. 15, the extraction facility includes a primary separation vessel (32) that receives the aforementioned slurry that is prepared by the mixing device and transported and conditioned by pipeline. In the PSV, the slurry undergoes gravity separation to produce a bitumen froth output stream (36), and a tailings output stream (38). The bitumen froth output stream (36) is further treated with solvent and subjected to separation processes to recover bitumen, while the tailings output may comprise a lost amount of bitumen.

The extraction facility operations generates the bitumen extraction process records, for a plurality of process times, indicative of the following information:

a process time (e.g., a date and time of operation of the PSV); and a bitumen recovery metric indicative of a rate or amount of bitumen recovery or loss for the bitumen extraction process at the one of the process times (e.g., a percentage of total bitumen loss to tailings or recovered from the bitumen froth, or an absolute weight or volume of bitumen loss to tailings or recovered from the bitumen froth).

The present invention is not limited by any particular manner by which the bitumen extraction process records are determined and acquired. As a non-limiting example, the process times may be determined as the times at which samples of tailings are acquired from the PSV. In embodiments, the process times may be "back-timed" to the earlier time at which the ore that produced a sample of tailings entered the PSV, based on a known residence time of slurry in the PSV, or a known time that the ore entered slurry preparation. The bitumen recovery metric may be determined from laboratory assays of the samples of tailings to determine a rate of bitumen loss to tailings.

The extraction facility operations may be associated with an extraction facility computer workstation (40) under control of an extraction facility operator such as an operator in control of diluent to the bitumen froth. The extraction facility computer workstation includes a display device (e.g., a computer monitor), and interacts with the system (1000) to generate on the display device the GUIs as described above.

System.

The system (1000) comprises a database, a computer processor, and a non-transitory computer readable medium. The system (1000) may be operatively connected (e.g., via one or more communication networks represented by dashed lines as shown in FIG. 15) with the computer workstations (18, 22, 40). In the embodiment shown in FIG. 15, the database and the non-transitory computer readable medium are collectively and notionally shown by a single storage icon (1002), and the computer processor is notionally shown by a single server icon (1004). However, despite such representation of the database, the non-transitory computer readable medium and the computer processor in FIG. 15, and their description herein in the singular for convenience, such computer components may comprise a plurality of operatively connected computer components which may be either physically integrated or physically remote from each other and in communication with each other via one or more communication networks.

A purpose of the database (1002) is to store the first and second database (5) of sets of ore characterization values and the second database or processability values, as derived from the characterization tests and processability tests performed on the core samples as described above, as well as the predictive ore processability model (6).

A purpose of the computer processor (1004) is to execute a set of instructions stored by the non-transitory computer readable medium to implement aspects of the method of the present invention, as described above. In an embodiment, the computer processor (1004) may comprise a web server—i.e., a computer processor responsive to requests from the computer workstations to display a web page. The non-transitory computer readable medium storing the set of instructions executable by the computer processor to implement a method of the present invention, may be considered independently of the computer processor (1004), to constitute a program product.

Through the use of the computer system (1000), it is possible to integrate the predictive ore processability model, with a geologic block model of an ore body, as well as mine site operations, mine planning operations, and the bitumen extraction process at the bitumen extraction facility. Conceivably, the system (1000) may even implement a semi-automated or automated feedback process whereby the bitumen extraction process records may be used to affect mine planning operations in the short-term (e.g., within a shift) to modify mine extraction operations with a view to controlling bitumen recovery and/or froth quality at the bitumen extraction facility. In addition, the system (1000) may implement a semi-automated or automated "feedforward" control whereby the predictive ore processability model may be used to predict the bitumen recovery and/or bitumen froth quality of ore characteristics of the blended ore feedstock produced from ore delivered from different ore locations, and the operating parameters of the bitumen extraction process may be adjusted with a view to controlling bitumen recovery and/or froth quality at the bitumen extraction facility.

Additional Interpretation.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such module, aspect, feature, structure, or characteristic with other embodiments, whether or not explicitly described. In other words, any module, element or feature may be combined with any other element or feature in different embodiments, unless there is an obvious or inherent incompatibility, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio.

The invention claimed is:

1. A method for predicting processability of an oil sands ore body in a bitumen extraction process, the method comprising the steps of:
   (a) obtaining core samples from a plurality of spatially separated locations within the ore body;
   (b) performing characterization tests on the core samples to establish a first database of sets of ore characteristic values comprising a bitumen content, a content of solid particles having a diameter less than 44 microns, and a content of ore formed in a marine depositional environment;
   (c) performing processability tests on the core samples to establish a second database of processability values indicative of any one or a combination of bitumen recovery from ore in the core samples in the bitumen extraction process, a bitumen content of bitumen froth in the bitumen extraction process, a solids content of bitumen froth in the bitumen extraction process, or a water content of bitumen froth in the bitumen extraction process, and
   (d) based on the first and second databases, determining a predictive ore processability model for predicting processability values from a specified set of ore characteristic values.

2. The method of claim 1, wherein the sets of ore characteristic values further comprise a water content.

3. The method of claim 1, wherein the sets of ore characteristic values further comprise a $50^{th}$ percentile solids particle size.

4. The method of claim 1, wherein the sets of ore characteristic values further comprise an aluminum content.

5. The method of claim 1, wherein the sets of ore characteristic values further comprise a pH level of connate water.

6. The method of claim 1, wherein the sets of ore characteristic values further comprise a water content, a $50^{th}$ percentile solids particle size, an aluminium content, a methylene blue index, a divalent cation content of connate water, a monovalent cation content of connate water, and a pH level of connate water.

7. The method of claim 1, wherein the sets of ore characteristic values further comprise a content of solid particles having a diameter less than 1.9 microns, and a $50^{th}$ percentile solids particle size.

8. The method of claim 1, wherein the sets of ore characteristic values further comprise the a content of solid particles having a diameter less than 1.9 microns, an aluminium content, a quartz content, a total clay content, an average critical surface tension, a chloride ion content in connate water, a sodium content in the connate water, a divalent ions content in connate water, a pH level of connate water, an electrolytic conductivity of connate water, and an asphaltene content of the bitumen.

9. The method of claim 1, wherein the sets of ore characteristic values further comprise a content of solid particles having a diameter less than 1.9 microns, a $50^{th}$ percentile solids particle size, an aluminium content, a calcium content, a iron content, a magnesium content, a silicon content, a percentage of ash remaining after heating of the core samples, a quartz content, a kaolinite content, an illite content, a total clay content, a methylene blue index, an average critical surface tension, a chloride ion content in connate water, a calcium content in connate water, an iron content in connate water, a potassium content in connate water, a magnesium content in connate water, a sodium content in connate water, a silicon content in connate water, a surfactant content in connate water, a pH level of connate water, an electrolytic conductivity of connate water, a sulphur content of the bitumen, an asphaltene content of the bitumen, and a microcarbon residue of the bitumen.

10. The method of claim 1, wherein the processability values are indicative of bitumen recovery from ore in the core samples in the bitumen extraction process.

11. The method of claim 1, wherein the processability values are indicative of the bitumen content of bitumen froth in the bitumen extraction process.

12. The method of claim 1, wherein the processability values are indicative of the solids content of bitumen froth in the bitumen extraction process.

13. The method of claim 1, wherein the processability values are indicative of the water content of bitumen froth in the bitumen extraction process.

14. The method of claim 1, wherein the predictive ore processability model comprises a rule correlating a range of ore characteristic values with a range of processability values.

15. The method of claim 14, wherein the rule is determined by using a computer implementing a pattern recognition algorithm.

16. The method of claim 1, wherein the method is further for controlling bitumen recovery from the oil sands ore body in the bitumen extraction process, the method further comprising the steps of:
   (e) incorporating the predictive ore processability model in a geologic block model of the ore body describing the ore characteristic values at block locations, to predict processability values for ore at the block locations; and
   (f) using the predicted processability values for ore at the block locations in determining planned amounts of ore deliveries from the block locations to a feed location of the bitumen extraction process within a time interval to produce a planned ore blend having a predicted bitumen recovery value within a predetermined range.

17. The method of claim 16, further comprising the step of:
- (g) based on the planned amounts, allocating mining equipment to the block locations to deliver ore from the block locations to a feed location to produce a blended ore feedstock for the bitumen extraction process.

18. The method of claim 17, wherein the method further comprises the steps of:
- (h) generating delivery records for ore deliveries to the feed location of the bitumen extraction process, within the time interval, wherein the delivery records comprise:
  - (i) information indicative of block locations from which the ore deliveries originated; and
  - (ii) actual amounts of the ore deliveries;
- (i) using a computer, generating a graphical user interface comprising:
  - (iii) a graphical representation of the planned amounts of ore deliveries from the block locations to the feed location within the time interval; and
  - (iv) a graphical representation of the actual amounts of ore deliveries from the block locations to the feed location within the time interval, based on the delivery records.

19. The method of claim 18, further comprising the steps of:
- (j) generating a bitumen extraction process record for an actual amount of bitumen recovered or lost from the feedstock; and
- (k) using the computer, generating the graphical user interface further comprising:
  - (i) a graphical representation of the actual amount of bitumen recovered or loss from the feedstock, based on the bitumen extraction process record.

20. The method of claim 1, further comprising the step of determining, based on the predictive ore processability model, an ore blending rule for the ore body that prescribes a combination of the ore characteristic values to achieve either a desired bitumen recovery or a desired bitumen froth quality, or both a desired bitumen recovery and a desired bitumen froth quality, from ore in the ore body in the bitumen extraction process.

21. The method of claim 1, further comprising the step of:
- (e) incorporating the ore characteristic values in a geologic block model of the ore body to describe the ore characteristic values at block locations;
- (f) generating delivery records for ore deliveries to a feed location of the bitumen extraction process, within a time interval, wherein the delivery records comprise:
  - (i) information indicative of block locations from which the ore deliveries originated; and
  - (ii) actual amounts of the ore deliveries;
- (g) based on the delivery records and the geologic block model of the ore body, determining a set of ore characteristic values for a blended ore feedstock produced by the ore deliveries to the feed location within the time interval; and
- (h) based on the predictive ore processability model, predicting the processability value for the determined set of ore characteristic values for the blended ore feedstock.

22. The method of claim 21, wherein the method is further for controlling bitumen recovery from the oil sands ore body in the bitumen extraction process, wherein the method further comprises the step of:
- (i) based on the predicted processability value for the determined set of the ore characteristic values for the blended ore feedstock, varying an operational parameter of the bitumen extraction process.

* * * * *